(12) United States Patent
Toth

(10) Patent No.: US 12,350,573 B2
(45) Date of Patent: Jul. 8, 2025

(54) SYSTEMS AND METHODS FOR CROSS-TRAINING ON EXERCISE DEVICES

(71) Applicant: iFIT Inc., Logan, UT (US)

(72) Inventor: Dawson Toth, Elkton, MD (US)

(73) Assignee: iFIT Inc., Logan, UT (US)

( * ) Notice: Subject to any disclaimer, the term of this patent is extended or adjusted under 35 U.S.C. 154(b) by 490 days.

(21) Appl. No.: 17/729,827

(22) Filed: Apr. 26, 2022

(65) Prior Publication Data
US 2022/0339520 A1     Oct. 27, 2022

Related U.S. Application Data

(60) Provisional application No. 63/180,458, filed on Apr. 27, 2021.

(51) Int. Cl.
*A63B 24/00* (2006.01)
*A63B 71/06* (2006.01)

(52) U.S. Cl.
CPC ...... *A63B 71/0622* (2013.01); *A63B 24/0062* (2013.01); *A63B 2225/15* (2013.01); *A63B 2225/20* (2013.01); *A63B 2225/50* (2013.01)

(58) Field of Classification Search
CPC ............ A63B 71/0622; A63B 24/0062; A63B 2225/15; A63B 2225/20; A63B 2225/50; A63B 21/225; A63B 22/0605; A63B 2022/0658; G16H 40/63; G16H 50/20; G16H 20/30
See application file for complete search history.

(56) References Cited

U.S. PATENT DOCUMENTS

| | | |
|---|---|---|
| 3,123,646 A | 3/1964 | Easton |
| 3,579,339 A | 5/1971 | Chang et al. |
| 4,023,795 A | 5/1977 | Pauls |
| 4,300,760 A | 11/1981 | Bobroff |
| D286,311 S | 10/1986 | Martinell et al. |
| 4,681,318 A | 7/1987 | Lay |
| 4,684,126 A | 8/1987 | Dalebout et al. |
| 4,728,102 A | 3/1988 | Pauls |
| 4,750,736 A | 6/1988 | Watterson |
| 4,796,881 A | 1/1989 | Watterson |

(Continued)

OTHER PUBLICATIONS

Roger Fingas: "Apple's GymKit: What it is, who supports it, and where you can find it," Apple Insider, Jun. 12, 2019, Retrieved from https://appleinsider.com/articles/19/06/12/apples-gymkit-what-it-is-who-supports-it-and-where-you-can-find-it, 17 pages.

(Continued)

*Primary Examiner* — Joshua Lee
*Assistant Examiner* — Catrina A Letterman
(74) *Attorney, Agent, or Firm* — Holland & Hart LLP

(57) ABSTRACT

A method of compiling workout information in a workout session includes, at a workout server, receiving, via a network, first login information from a first exercise device; receiving, via the network, first workout information from the first exercise device; recording the first workout information in an active workout session; receiving, via the network, second login information from a second exercise device; receiving, via the network, second workout information from the second exercise device; and recording the second workout information in the active workout session.

19 Claims, 5 Drawing Sheets

(56) References Cited

U.S. PATENT DOCUMENTS

| | | |
|---|---|---|
| 4,813,667 A | 3/1989 | Watterson |
| 4,830,371 A | 5/1989 | Lay |
| 4,844,451 A | 7/1989 | Bersonnet et al. |
| 4,850,585 A | 7/1989 | Dalebout et al. |
| D304,849 S | 11/1989 | Watterson |
| 4,880,225 A | 11/1989 | Lucas et al. |
| 4,883,272 A | 11/1989 | Lay |
| D306,468 S | 3/1990 | Watterson |
| D306,891 S | 3/1990 | Watterson |
| 4,913,396 A | 4/1990 | Dalebout et al. |
| D307,614 S | 5/1990 | Bingham et al. |
| D307,615 S | 5/1990 | Bingham et al. |
| 4,921,242 A | 5/1990 | Watterson |
| 4,932,650 A | 6/1990 | Bingham et al. |
| D309,167 S | 7/1990 | Griffin |
| D309,485 S | 7/1990 | Bingham et al. |
| 4,938,478 A | 7/1990 | Lay |
| D310,253 S | 8/1990 | Bersonnet et al. |
| 4,955,599 A | 9/1990 | Bersonnet et al. |
| 4,971,316 A | 11/1990 | Dalebout et al. |
| D313,055 S | 12/1990 | Watterson |
| 4,974,832 A | 12/1990 | Dalebout |
| 4,979,737 A | 12/1990 | Kock |
| 4,981,294 A | 1/1991 | Dalebout et al. |
| D315,765 S | 3/1991 | Measom et al. |
| 4,998,725 A | 3/1991 | Watterson et al. |
| 5,000,442 A | 3/1991 | Dalebout et al. |
| 5,000,443 A | 3/1991 | Dalebout et al. |
| 5,000,444 A | 3/1991 | Dalebout et al. |
| D316,124 S | 4/1991 | Dalebout et al. |
| 5,013,033 A | 5/1991 | Watterson et al. |
| 5,014,980 A | 5/1991 | Bersonnet et al. |
| 5,016,871 A | 5/1991 | Dalebout et al. |
| D318,085 S | 7/1991 | Jacobson et al. |
| D318,086 S | 7/1991 | Bingham et al. |
| D318,699 S | 7/1991 | Jacobson et al. |
| 5,029,801 A | 7/1991 | Dalebout et al. |
| 5,034,576 A | 7/1991 | Dalebout et al. |
| 5,058,881 A | 10/1991 | Measom |
| 5,058,882 A | 10/1991 | Dalebout et al. |
| D321,388 S | 11/1991 | Dalebout |
| 5,062,626 A | 11/1991 | Dalebout et al. |
| 5,062,627 A | 11/1991 | Bingham |
| 5,062,632 A | 11/1991 | Dalebout et al. |
| 5,062,633 A | 11/1991 | Engel et al. |
| 5,067,710 A | 11/1991 | Watterson et al. |
| 5,072,929 A | 12/1991 | Peterson et al. |
| D323,009 S | 1/1992 | Dalebout et al. |
| D323,198 S | 1/1992 | Dalebout et al. |
| D323,199 S | 1/1992 | Dalebout et al. |
| D323,863 S | 2/1992 | Watterson |
| 5,088,729 A | 2/1992 | Dalebout |
| 5,090,694 A | 2/1992 | Pauls et al. |
| 5,102,380 A | 4/1992 | Jacobson et al. |
| 5,104,120 A | 4/1992 | Watterson et al. |
| 5,108,093 A | 4/1992 | Watterson |
| D326,491 S | 5/1992 | Dalebout |
| 5,122,105 A | 6/1992 | Engel et al. |
| 5,135,216 A | 8/1992 | Bingham et al. |
| 5,147,265 A | 9/1992 | Pauls et al. |
| 5,149,084 A | 9/1992 | Dalebout et al. |
| 5,149,312 A | 9/1992 | Croft et al. |
| 5,171,196 A | 12/1992 | Lynch |
| D332,347 S | 1/1993 | Raadt et al. |
| 5,190,505 A | 3/1993 | Dalebout et al. |
| 5,192,255 A | 3/1993 | Dalebout et al. |
| 5,195,937 A | 3/1993 | Engel et al. |
| 5,203,826 A | 4/1993 | Dalebout |
| D335,511 S | 5/1993 | Engel et al. |
| D335,905 S | 5/1993 | Cutter et al. |
| D336,498 S | 6/1993 | Engel et al. |
| 5,217,487 A | 6/1993 | Engel et al. |
| D337,361 S | 7/1993 | Engel et al. |
| D337,666 S | 7/1993 | Peterson et al. |
| D337,799 S | 7/1993 | Cutter et al. |
| 5,226,866 A | 7/1993 | Engel et al. |
| 5,244,446 A | 9/1993 | Engel et al. |
| 5,247,853 A | 9/1993 | Dalebout |
| 5,259,611 A | 11/1993 | Dalebout et al. |
| D342,106 S | 12/1993 | Campbell et al. |
| 5,279,528 A | 1/1994 | Dalebout et al. |
| D344,112 S | 2/1994 | Smith |
| D344,557 S | 2/1994 | Ashby |
| 5,282,776 A | 2/1994 | Dalebout |
| 5,295,931 A | 3/1994 | Dreibelbis et al. |
| 5,302,161 A | 4/1994 | Loubert et al. |
| D347,251 S | 5/1994 | Dreibelbis et al. |
| 5,316,534 A | 5/1994 | Dalebout et al. |
| D348,493 S | 7/1994 | Ashby |
| D348,494 S | 7/1994 | Ashby |
| 5,328,164 A | 7/1994 | Soga |
| D349,931 S | 8/1994 | Bostic et al. |
| 5,336,142 A | 8/1994 | Dalebout et al. |
| 5,344,376 A | 9/1994 | Bostic et al. |
| D351,202 S | 10/1994 | Bingham |
| D351,435 S | 10/1994 | Peterson et al. |
| D351,633 S | 10/1994 | Bingham |
| D352,534 S | 11/1994 | Dreibelbis et al. |
| D353,422 S | 12/1994 | Bostic et al. |
| 5,372,559 A | 12/1994 | Dalebout et al. |
| 5,374,228 A | 12/1994 | Buisman et al. |
| 5,382,221 A | 1/1995 | Hsu et al. |
| 5,387,168 A | 2/1995 | Bostic |
| 5,393,690 A | 2/1995 | Fu et al. |
| D356,128 S | 3/1995 | Smith et al. |
| 5,409,435 A | 4/1995 | Daniels |
| 5,429,563 A | 7/1995 | Engel et al. |
| 5,431,612 A | 7/1995 | Holden |
| D360,915 S | 8/1995 | Bostic et al. |
| 5,468,205 A | 11/1995 | McFall et al. |
| 5,489,249 A | 2/1996 | Brewer et al. |
| 5,492,517 A | 2/1996 | Bostic et al. |
| D367,689 S | 3/1996 | Wilkinson et al. |
| 5,511,740 A | 4/1996 | Loubert et al. |
| 5,512,025 A | 4/1996 | Dalebout et al. |
| D370,949 S | 6/1996 | Furner |
| D371,176 S | 6/1996 | Furner |
| 5,527,245 A | 6/1996 | Dalebout et al. |
| 5,529,553 A | 6/1996 | Finlayson |
| 5,540,429 A | 7/1996 | Dalebout et al. |
| 5,549,533 A | 8/1996 | Olson et al. |
| 5,554,085 A | 9/1996 | Dalebout |
| 5,569,128 A | 10/1996 | Dalebout |
| 5,591,105 A | 1/1997 | Dalebout et al. |
| 5,591,106 A | 1/1997 | Dalebout et al. |
| 5,595,556 A | 1/1997 | Dalebout et al. |
| 5,607,375 A | 3/1997 | Dalebout et al. |
| 5,611,539 A | 3/1997 | Watterson et al. |
| 5,622,527 A | 4/1997 | Watterson et al. |
| 5,626,538 A | 5/1997 | Dalebout et al. |
| 5,626,542 A | 5/1997 | Dalebout et al. |
| D380,024 S | 6/1997 | Novak et al. |
| 5,637,059 A | 6/1997 | Dalebout |
| D380,509 S | 7/1997 | Wilkinson et al. |
| 5,643,153 A | 7/1997 | Nylen et al. |
| 5,645,509 A | 7/1997 | Brewer et al. |
| D384,118 S | 9/1997 | Deblauw |
| 5,662,557 A | 9/1997 | Watterson et al. |
| 5,669,857 A | 9/1997 | Watterson et al. |
| 5,672,140 A | 9/1997 | Watterson et al. |
| 5,674,156 A | 10/1997 | Watterson et al. |
| 5,674,453 A | 10/1997 | Watterson et al. |
| 5,676,624 A | 10/1997 | Watterson et al. |
| 5,683,331 A | 11/1997 | Dalebout |
| 5,683,332 A | 11/1997 | Watterson et al. |
| D387,825 S | 12/1997 | Fleck et al. |
| 5,695,433 A | 12/1997 | Buisman |
| 5,695,434 A | 12/1997 | Dalebout et al. |
| 5,695,435 A | 12/1997 | Dalebout et al. |
| 5,702,325 A | 12/1997 | Watterson et al. |
| 5,704,879 A | 1/1998 | Watterson et al. |
| 5,718,657 A | 2/1998 | Dalebout et al. |
| 5,720,200 A | 2/1998 | Anderson et al. |
| 5,720,698 A | 2/1998 | Dalebout et al. |

(56) References Cited

U.S. PATENT DOCUMENTS

| | | | |
|---|---|---|---|
| D392,006 S | 3/1998 | Dalebout et al. |
| 5,722,922 A | 3/1998 | Watterson et al. |
| 5,733,229 A | 3/1998 | Dalebout et al. |
| 5,743,833 A | 4/1998 | Watterson et al. |
| 5,762,584 A | 6/1998 | Daniels |
| 5,762,587 A | 6/1998 | Dalebout et al. |
| 5,772,560 A | 6/1998 | Watterson et al. |
| 5,810,698 A | 9/1998 | Hullett et al. |
| 5,827,155 A | 10/1998 | Jensen et al. |
| 5,830,114 A | 11/1998 | Halfen et al. |
| 5,860,893 A | 1/1999 | Watterson et al. |
| 5,860,894 A | 1/1999 | Dalebout et al. |
| 5,899,834 A | 5/1999 | Dalebout et al. |
| D412,953 S | 8/1999 | Armstrong |
| D413,948 S | 9/1999 | Dalebout |
| 5,951,441 A | 9/1999 | Dalebout et al. |
| 5,951,448 A | 9/1999 | Bolland |
| D416,596 S | 11/1999 | Armstrong |
| 6,003,166 A | 12/1999 | Hald et al. |
| 6,019,710 A | 2/2000 | Dalebout et al. |
| 6,027,429 A | 2/2000 | Daniels |
| 6,033,347 A | 3/2000 | Dalebout et al. |
| D425,940 S | 5/2000 | Halfen et al. |
| 6,059,692 A | 5/2000 | Hickman |
| D428,949 S | 8/2000 | Simonson |
| 6,123,646 A | 9/2000 | Colassi |
| 6,171,217 B1 | 1/2001 | Cutler |
| 6,171,219 B1 | 1/2001 | Simonson |
| 6,174,267 B1 | 1/2001 | Dalebout et al. |
| 6,193,631 B1 | 2/2001 | Hickman |
| 6,228,003 B1 | 5/2001 | Hald et al. |
| 6,238,323 B1 | 5/2001 | Simonson |
| 6,251,052 B1 | 6/2001 | Simonson |
| 6,261,022 B1 | 7/2001 | Dalebout et al. |
| 6,280,362 B1 | 8/2001 | Dalebout et al. |
| 6,296,594 B1 | 10/2001 | Simonson |
| D450,872 S | 11/2001 | Dalebout et al. |
| 6,312,363 B1 | 11/2001 | Watterson et al. |
| D452,338 S | 12/2001 | Dalebout et al. |
| D453,543 S | 2/2002 | Cutler |
| D453,948 S | 2/2002 | Cutler |
| 6,350,218 B1 | 2/2002 | Dalebout et al. |
| 6,387,020 B1 | 5/2002 | Simonson |
| 6,413,191 B1 | 7/2002 | Harris et al. |
| 6,422,980 B1 | 7/2002 | Simonson |
| 6,447,424 B1 | 9/2002 | Ashby et al. |
| 6,458,060 B1 | 10/2002 | Watterson et al. |
| 6,458,061 B2 | 10/2002 | Simonson |
| 6,471,622 B1 | 10/2002 | Hammer et al. |
| 6,563,225 B2 | 5/2003 | Soga et al. |
| 6,601,016 B1 * | 7/2003 | Brown ............... A63B 24/0062 |
| | | 702/182 |
| 6,623,140 B2 | 9/2003 | Watterson et al. |
| 6,626,799 B2 | 9/2003 | Watterson et al. |
| 6,652,424 B2 | 11/2003 | Dalebout |
| 6,685,607 B1 | 2/2004 | Olson |
| 6,695,581 B2 | 2/2004 | Wasson et al. |
| 6,701,271 B2 | 3/2004 | Willner et al. |
| 6,702,719 B1 * | 3/2004 | Brown ................... G16H 10/60 |
| | | 482/4 |
| 6,712,740 B2 | 3/2004 | Simonson |
| 6,730,002 B2 | 5/2004 | Hald et al. |
| 6,743,153 B2 | 6/2004 | Watterson et al. |
| 6,746,371 B1 | 6/2004 | Brown et al. |
| 6,749,537 B1 | 6/2004 | Hickman |
| 6,761,667 B1 | 7/2004 | Cutler et al. |
| 6,770,015 B2 | 8/2004 | Simonson |
| 6,786,852 B2 | 9/2004 | Watterson et al. |
| 6,808,472 B1 | 10/2004 | Hickman |
| 6,821,230 B2 | 11/2004 | Dalebout et al. |
| 6,830,540 B2 | 12/2004 | Watterson et al. |
| 6,863,641 B1 | 3/2005 | Brown et al. |
| 6,866,613 B1 | 3/2005 | Brown et al. |
| 6,875,160 B2 | 4/2005 | Watterson et al. |
| D507,311 S | 7/2005 | Butler et al. |
| 6,918,858 B2 | 7/2005 | Watterson et al. |
| 6,921,351 B1 | 7/2005 | Hickman et al. |
| 6,974,404 B1 | 12/2005 | Watterson et al. |
| 6,997,852 B2 | 2/2006 | Watterson et al. |
| 7,025,713 B2 | 4/2006 | Dalebout et al. |
| D520,085 S | 5/2006 | Willardson et al. |
| 7,044,897 B2 | 5/2006 | Myers et al. |
| 7,052,442 B2 | 5/2006 | Watterson et al. |
| 7,060,006 B1 | 6/2006 | Watterson et al. |
| 7,060,008 B2 | 6/2006 | Watterson et al. |
| 7,070,539 B2 | 7/2006 | Brown et al. |
| 7,097,588 B2 | 8/2006 | Watterson et al. |
| D527,776 S | 9/2006 | Willardson et al. |
| 7,112,168 B2 | 9/2006 | Dalebout et al. |
| 7,128,693 B2 | 10/2006 | Brown et al. |
| 7,166,062 B1 | 1/2007 | Watterson et al. |
| 7,166,064 B2 | 1/2007 | Watterson et al. |
| 7,169,087 B2 | 1/2007 | Ercanbrack et al. |
| 7,169,093 B2 | 1/2007 | Simonson et al. |
| 7,192,388 B2 | 3/2007 | Dalebout et al. |
| 7,250,022 B2 | 7/2007 | Dalebout et al. |
| 7,282,016 B2 | 10/2007 | Simonson |
| 7,285,075 B2 | 10/2007 | Cutler et al. |
| 7,344,481 B2 | 3/2008 | Watterson et al. |
| 7,377,882 B2 | 5/2008 | Watterson et al. |
| 7,425,188 B2 | 9/2008 | Ercanbrack et al. |
| 7,429,236 B2 | 9/2008 | Dalebout et al. |
| 7,455,622 B2 | 11/2008 | Watterson et al. |
| 7,482,050 B2 | 1/2009 | Olson |
| D588,655 S | 3/2009 | Utykanski |
| 7,510,509 B2 | 3/2009 | Hickman |
| 7,537,546 B2 | 5/2009 | Watterson et al. |
| 7,537,549 B2 | 5/2009 | Nelson et al. |
| 7,537,552 B2 | 5/2009 | Dalebout et al. |
| 7,540,828 B2 | 6/2009 | Watterson et al. |
| 7,549,947 B2 | 6/2009 | Hickman et al. |
| 7,556,590 B2 | 7/2009 | Watterson et al. |
| 7,563,203 B2 | 7/2009 | Dalebout et al. |
| 7,575,536 B1 | 8/2009 | Hickman |
| 7,601,105 B1 | 10/2009 | Gipson et al. |
| 7,604,573 B2 | 10/2009 | Dalebout et al. |
| D604,373 S | 11/2009 | Dalebout et al. |
| 7,618,350 B2 | 11/2009 | Dalebout et al. |
| 7,618,357 B2 | 11/2009 | Dalebout et al. |
| 7,625,315 B2 | 12/2009 | Hickman |
| 7,625,321 B2 | 12/2009 | Simonson et al. |
| 7,628,730 B1 | 12/2009 | Watterson et al. |
| 7,628,737 B2 | 12/2009 | Kowallis et al. |
| 7,637,847 B1 | 12/2009 | Hickman |
| 7,645,212 B2 | 1/2010 | Ashby et al. |
| 7,645,213 B2 | 1/2010 | Watterson et al. |
| 7,658,698 B2 | 2/2010 | Pacheco et al. |
| 7,674,205 B2 | 3/2010 | Dalebout et al. |
| 7,713,171 B1 | 5/2010 | Hickman |
| 7,713,172 B2 | 5/2010 | Watterson et al. |
| 7,713,180 B2 | 5/2010 | Wickens et al. |
| 7,717,828 B2 | 5/2010 | Simonson et al. |
| 7,736,279 B2 | 6/2010 | Dalebout et al. |
| 7,740,563 B2 | 6/2010 | Dalebout et al. |
| 7,749,144 B2 | 7/2010 | Hammer |
| 7,766,797 B2 | 8/2010 | Dalebout et al. |
| 7,771,329 B2 | 8/2010 | Dalebout et al. |
| 7,775,940 B2 | 8/2010 | Dalebout et al. |
| 7,789,800 B1 | 9/2010 | Watterson et al. |
| 7,798,946 B2 | 9/2010 | Dalebout et al. |
| 7,815,550 B2 | 10/2010 | Watterson et al. |
| 7,857,731 B2 | 12/2010 | Hickman et al. |
| 7,862,475 B2 | 1/2011 | Watterson et al. |
| 7,862,478 B2 | 1/2011 | Watterson et al. |
| 7,862,483 B2 | 1/2011 | Hendrickson et al. |
| D635,207 S | 3/2011 | Dalebout et al. |
| 7,901,330 B2 | 3/2011 | Dalebout et al. |
| 7,909,740 B2 | 3/2011 | Dalebout et al. |
| 7,980,996 B2 | 7/2011 | Hickman |
| 7,981,000 B2 | 7/2011 | Watterson et al. |
| 7,985,164 B2 | 7/2011 | Ashby |
| 8,029,415 B2 | 10/2011 | Ashby et al. |
| 8,033,960 B1 | 10/2011 | Dalebout et al. |
| D650,451 S | 12/2011 | Olson et al. |

(56) References Cited

U.S. PATENT DOCUMENTS

| | | |
|---|---|---|
| D652,877 S | 1/2012 | Dalebout et al. |
| 8,152,702 B2 | 4/2012 | Pacheco |
| D659,775 S | 5/2012 | Olson et al. |
| D659,777 S | 5/2012 | Watterson et al. |
| D660,383 S | 5/2012 | Watterson et al. |
| D664,613 S | 7/2012 | Dalebout et al. |
| 8,251,874 B2 | 8/2012 | Ashby et al. |
| 8,298,123 B2 | 10/2012 | Hickman |
| 8,298,125 B2 | 10/2012 | Colledge et al. |
| D671,177 S | 11/2012 | Sip |
| D671,178 S | 11/2012 | Sip |
| D673,626 S | 1/2013 | Olson et al. |
| 8,690,735 B2 | 4/2014 | Watterson et al. |
| D707,763 S | 6/2014 | Cutler |
| 8,740,753 B2 | 6/2014 | Olson et al. |
| 8,758,201 B2 | 6/2014 | Ashby et al. |
| 8,771,153 B2 | 7/2014 | Dalebout et al. |
| 8,784,270 B2 | 7/2014 | Ashby et al. |
| 8,808,148 B2 | 8/2014 | Watterson et al. |
| 8,814,762 B2 | 8/2014 | Butler et al. |
| D712,493 S | 9/2014 | Ercanbrack et al. |
| 8,840,075 B2 | 9/2014 | Dalebout et al. |
| 8,845,493 B2 | 9/2014 | Watterson et al. |
| 8,870,726 B2 | 10/2014 | Watterson et al. |
| 8,876,668 B2 | 11/2014 | Hendrickson et al. |
| 8,894,549 B2 | 11/2014 | Colledge |
| 8,894,555 B2 | 11/2014 | Colledge et al. |
| 8,911,330 B2 | 12/2014 | Watterson et al. |
| 8,920,288 B2 | 12/2014 | Dalebout et al. |
| 8,986,165 B2 | 3/2015 | Ashby |
| 8,992,364 B2 | 3/2015 | Law et al. |
| 8,992,387 B2 | 3/2015 | Watterson et al. |
| D726,476 S | 4/2015 | Ercanbrack |
| 9,028,368 B2 | 5/2015 | Ashby et al. |
| 9,028,370 B2 | 5/2015 | Watterson et al. |
| 9,039,578 B2 | 5/2015 | Dalebout |
| D731,011 S | 6/2015 | Buchanan |
| 9,072,930 B2 | 7/2015 | Ashby et al. |
| 9,119,983 B2 | 9/2015 | Rhea |
| 9,123,317 B2 | 9/2015 | Watterson et al. |
| 9,126,071 B2 | 9/2015 | Smith |
| 9,126,072 B2 | 9/2015 | Watterson |
| 9,138,615 B2 | 9/2015 | Olson et al. |
| 9,142,139 B2 | 9/2015 | Watterson et al. |
| 9,144,703 B2 | 9/2015 | Dalebout et al. |
| 9,149,683 B2 | 10/2015 | Watterson et al. |
| 9,186,535 B2 | 11/2015 | Ercanbrack |
| 9,186,549 B2 | 11/2015 | Watterson et al. |
| 9,254,409 B2 | 2/2016 | Dalebout et al. |
| 9,254,416 B2 | 2/2016 | Ashby |
| 9,278,248 B2 | 3/2016 | Tyger et al. |
| 9,278,249 B2 | 3/2016 | Watterson |
| 9,278,250 B2 | 3/2016 | Buchanan |
| 9,289,648 B2 | 3/2016 | Watterson |
| 9,339,691 B2 | 5/2016 | Brammer |
| 9,352,185 B2 | 5/2016 | Hendrickson et al. |
| 9,352,186 B2 | 5/2016 | Watterson |
| 9,375,605 B2 | 6/2016 | Tyger et al. |
| 9,381,394 B2 | 7/2016 | Mortensen et al. |
| 9,387,387 B2 | 7/2016 | Dalebout |
| 9,393,453 B2 | 7/2016 | Watterson |
| 9,403,047 B2 | 8/2016 | Olson et al. |
| 9,403,051 B2 | 8/2016 | Cutler |
| 9,421,416 B2 | 8/2016 | Mortensen et al. |
| 9,457,219 B2 | 10/2016 | Smith |
| 9,457,220 B2 | 10/2016 | Olson |
| 9,457,222 B2 | 10/2016 | Dalebout |
| 9,460,632 B2 | 10/2016 | Watterson |
| 9,463,356 B2 | 10/2016 | Rhea |
| 9,468,794 B2 | 10/2016 | Barton |
| 9,468,798 B2 | 10/2016 | Dalebout |
| 9,480,874 B2 | 11/2016 | Cutler |
| 9,492,704 B2 | 11/2016 | Mortensen et al. |
| 9,498,668 B2 | 11/2016 | Smith |
| 9,517,378 B2 | 12/2016 | Ashby et al. |
| 9,521,901 B2 | 12/2016 | Dalebout |
| 9,533,187 B2 | 1/2017 | Dalebout |
| 9,539,461 B2 | 1/2017 | Ercanbrack |
| 9,579,544 B2 | 2/2017 | Watterson |
| 9,586,086 B2 | 3/2017 | Dalebout et al. |
| 9,586,090 B2 | 3/2017 | Watterson et al. |
| 9,604,099 B2 | 3/2017 | Taylor |
| 9,616,276 B2 | 4/2017 | Dalebout et al. |
| 9,616,278 B2 | 4/2017 | Olson |
| 9,623,281 B2 | 4/2017 | Hendrickson et al. |
| 9,636,567 B2 | 5/2017 | Brammer et al. |
| 9,675,839 B2 | 6/2017 | Dalebout et al. |
| 9,682,307 B2 | 6/2017 | Dalebout |
| 9,694,234 B2 | 7/2017 | Dalebout et al. |
| 9,694,242 B2 | 7/2017 | Ashby et al. |
| 9,737,755 B2 | 8/2017 | Dalebout |
| 9,757,605 B2 | 9/2017 | Olson et al. |
| 9,764,186 B2 | 9/2017 | Dalebout et al. |
| 9,767,785 B2 | 9/2017 | Ashby et al. |
| 9,795,822 B2 | 10/2017 | Smith et al. |
| 9,808,672 B2 | 11/2017 | Dalebout |
| 9,849,326 B2 | 12/2017 | Smith |
| 9,878,210 B2 | 1/2018 | Watterson |
| 9,889,334 B2 | 2/2018 | Ashby et al. |
| 9,889,339 B2 | 2/2018 | Douglass |
| 9,937,376 B2 | 4/2018 | McInelly et al. |
| 9,937,377 B2 | 4/2018 | McInelly et al. |
| 9,937,378 B2 | 4/2018 | Dalebout et al. |
| 9,937,379 B2 | 4/2018 | Mortensen et al. |
| 9,943,719 B2 | 4/2018 | Smith et al. |
| 9,943,722 B2 | 4/2018 | Dalebout |
| 9,948,037 B2 | 4/2018 | Ashby |
| 9,968,816 B2 | 5/2018 | Olson et al. |
| 9,968,821 B2 | 5/2018 | Finlayson et al. |
| 9,968,823 B2 | 5/2018 | Cutler |
| 10,010,755 B2 | 7/2018 | Watterson |
| 10,010,756 B2 | 7/2018 | Watterson |
| 10,029,145 B2 | 7/2018 | Douglass |
| D826,350 S | 8/2018 | Hochstrasser |
| 10,046,196 B2 | 8/2018 | Ercanbrack et al. |
| D827,733 S | 9/2018 | Hochstrasser |
| 10,065,064 B2 | 9/2018 | Smith et al. |
| 10,071,285 B2 | 9/2018 | Smith et al. |
| 10,085,586 B2 | 10/2018 | Smith et al. |
| 10,086,254 B2 | 10/2018 | Watterson |
| 10,136,842 B2 | 11/2018 | Ashby |
| 10,186,161 B2 | 1/2019 | Watterson |
| 10,188,890 B2 | 1/2019 | Olson et al. |
| 10,207,143 B2 | 2/2019 | Dalebout et al. |
| 10,207,145 B2 | 2/2019 | Tyger et al. |
| 10,207,147 B2 | 2/2019 | Ercanbrack et al. |
| 10,207,148 B2 | 2/2019 | Powell et al. |
| 10,212,994 B2 | 2/2019 | Watterson et al. |
| 10,220,259 B2 | 3/2019 | Brammer |
| 10,226,396 B2 | 3/2019 | Ashby |
| 10,226,664 B2 | 3/2019 | Dalebout et al. |
| 10,252,109 B2 | 4/2019 | Watterson |
| 10,258,828 B2 | 4/2019 | Dalebout et al. |
| 10,272,317 B2 | 4/2019 | Watterson |
| 10,279,212 B2 | 5/2019 | Dalebout et al. |
| 10,293,211 B2 | 5/2019 | Watterson et al. |
| D852,292 S | 6/2019 | Cutler |
| 10,343,017 B2 | 7/2019 | Jackson |
| 10,376,736 B2 | 8/2019 | Powell et al. |
| 10,388,183 B2 | 8/2019 | Watterson |
| 10,391,361 B2 | 8/2019 | Watterson |
| D864,320 S | 10/2019 | Weston |
| D864,321 S | 10/2019 | Weston |
| 10,426,989 B2 | 10/2019 | Dalebout |
| 10,433,612 B2 | 10/2019 | Ashby et al. |
| 10,441,840 B2 | 10/2019 | Dalebout |
| 10,441,844 B2 | 10/2019 | Powell |
| 10,449,416 B2 | 10/2019 | Dalebout et al. |
| 10,471,299 B2 | 11/2019 | Powell |
| D868,909 S | 12/2019 | Cutler et al. |
| 10,492,519 B2 | 12/2019 | Capell et al. |
| 10,493,349 B2 | 12/2019 | Watterson |
| 10,500,473 B2 | 12/2019 | Watterson |
| 10,537,764 B2 | 1/2020 | Smith et al. |

(56) References Cited

U.S. PATENT DOCUMENTS

| | | |
|---|---|---|
| 10,543,395 B2 | 1/2020 | Powell et al. |
| 10,561,877 B2 | 2/2020 | Workman |
| 10,561,893 B2 | 2/2020 | Chatterton et al. |
| 10,561,894 B2 | 2/2020 | Dalebout et al. |
| 10,569,121 B2 | 2/2020 | Watterson |
| 10,569,123 B2 | 2/2020 | Hochstrasser et al. |
| 10,625,114 B2 | 4/2020 | Ercanbrack |
| 10,625,137 B2 | 4/2020 | Dalebout et al. |
| 10,661,114 B2 | 5/2020 | Watterson et al. |
| 10,668,320 B2 | 6/2020 | Watterson |
| 10,671,705 B2 | 6/2020 | Capell et al. |
| 10,688,346 B2 | 6/2020 | Brammer |
| 10,702,736 B2 | 7/2020 | Weston et al. |
| 10,709,925 B2 | 7/2020 | Dalebout et al. |
| 10,726,730 B2 | 7/2020 | Watterson |
| 10,729,965 B2 | 8/2020 | Powell |
| 10,758,767 B2 | 9/2020 | Olson et al. |
| 10,786,706 B2 | 9/2020 | Smith |
| 10,864,407 B2 | 12/2020 | Watterson et al. |
| 10,918,905 B2 | 2/2021 | Powell et al. |
| 10,932,517 B2 | 3/2021 | Ashby et al. |
| 10,940,360 B2 | 3/2021 | Dalebout et al. |
| 10,953,268 B1 | 3/2021 | Dalebout et al. |
| 10,953,305 B2 | 3/2021 | Dalebout et al. |
| 10,967,214 B1 | 4/2021 | Olson et al. |
| 10,994,173 B2 | 5/2021 | Watterson |
| 11,000,730 B2 | 5/2021 | Dalebout et al. |
| 11,013,960 B2 | 5/2021 | Watterson et al. |
| 11,033,777 B1 | 6/2021 | Watterson et al. |
| 11,058,913 B2 | 7/2021 | Dalebout et al. |
| 11,058,914 B2 | 7/2021 | Powell |
| 11,058,918 B1 | 7/2021 | Watterson et al. |
| 11,187,285 B2 | 11/2021 | Wrobel |
| 11,298,577 B2 | 4/2022 | Watterson |
| 11,326,673 B2 | 5/2022 | Buchanan |
| 11,338,169 B2 | 5/2022 | Dalebout et al. |
| 11,338,175 B2 * | 5/2022 | Watterson ............... G16H 40/63 |
| 11,426,633 B2 | 8/2022 | Watterson et al. |
| 11,451,108 B2 | 9/2022 | Tinney |
| 11,452,903 B2 | 9/2022 | Watterson |
| 11,511,152 B2 | 11/2022 | Powell et al. |
| 11,534,651 B2 | 12/2022 | Ercanbrack et al. |
| 11,534,654 B2 | 12/2022 | Silcock et al. |
| 11,534,655 B2 | 12/2022 | Dalebout et al. |
| 11,565,148 B2 | 1/2023 | Dalebout et al. |
| 11,596,830 B2 | 3/2023 | Dalebout et al. |
| 11,642,564 B2 | 5/2023 | Watterson |
| 11,673,036 B2 | 6/2023 | Dalebout et al. |
| 11,680,611 B2 | 6/2023 | Wrobel |
| 11,700,905 B2 | 7/2023 | Ashby et al. |
| 11,708,874 B2 | 7/2023 | Wrobel |
| 2001/0004622 A1 * | 6/2001 | Alessandri ............ G16H 40/63 482/8 |
| 2004/0077462 A1 * | 4/2004 | Brown ................. A63F 13/323 482/8 |
| 2008/0051256 A1 | 2/2008 | Ashby et al. |
| 2009/0219159 A1 * | 9/2009 | Morgenstern .......... A63B 24/00 340/10.42 |
| 2015/0251055 A1 | 9/2015 | Ashby |
| 2017/0124912 A1 | 5/2017 | Ashby et al. |
| 2017/0193578 A1 | 7/2017 | Watterson |
| 2017/0266489 A1 | 9/2017 | Douglass et al. |
| 2017/0270820 A1 | 9/2017 | Ashby et al. |
| 2018/0085630 A1 | 3/2018 | Capell et al. |
| 2018/0099116 A1 | 4/2018 | Ashby |
| 2018/0099180 A1 | 4/2018 | Wilkinson |
| 2018/0111034 A1 | 4/2018 | Watterson |
| 2019/0223612 A1 | 7/2019 | Watterson et al. |
| 2019/0269971 A1 | 9/2019 | Capell et al. |
| 2020/0009417 A1 | 1/2020 | Dalebout |
| 2020/0391069 A1 | 8/2020 | Olson et al. |
| 2020/0368575 A1 | 11/2020 | Hays et al. |
| 2021/0001177 A1 | 1/2021 | Smith |
| 2021/0046353 A1 | 2/2021 | Dalebout et al. |
| 2021/0106899 A1 | 4/2021 | Willardson et al. |
| 2021/0110910 A1 | 4/2021 | Ostler et al. |
| 2021/0146221 A1 | 5/2021 | Dalebout et al. |
| 2021/0213331 A1 | 7/2021 | Watterson |
| 2021/0268336 A1 | 9/2021 | Watterson et al. |
| 2021/0291013 A1 | 9/2021 | Nascimento |
| 2021/0299518 A1 | 9/2021 | Brammer et al. |
| 2021/0299542 A1 | 9/2021 | Brammer et al. |
| 2021/0339079 A1 | 11/2021 | Dalebout et al. |
| 2022/0062685 A1 | 3/2022 | Ashby et al. |
| 2022/0104992 A1 | 4/2022 | Ashby |
| 2022/0212052 A1 | 7/2022 | Ercanbrack et al. |
| 2022/0241649 A1 | 8/2022 | Ashby |
| 2022/0241665 A1 | 8/2022 | Dalebout et al. |
| 2022/0241668 A1 | 8/2022 | Willardson et al. |
| 2022/0249912 A1 | 8/2022 | Watterson et al. |
| 2022/0257994 A1 | 8/2022 | Smith |
| 2022/0258007 A1 | 8/2022 | Watterson et al. |
| 2022/0258008 A1 | 8/2022 | Watterson et al. |
| 2022/0266085 A1 | 8/2022 | Dalebout et al. |
| 2022/0280857 A1 | 9/2022 | Watterson |
| 2022/0309042 A1 | 9/2022 | Archer |
| 2022/0314078 A1 | 10/2022 | Watterson et al. |
| 2022/0323827 A1 | 10/2022 | Watterson et al. |
| 2022/0339493 A1 | 10/2022 | Larsen |
| 2022/0339520 A1 | 10/2022 | Toth |
| 2022/0342969 A1 | 10/2022 | Watterson et al. |
| 2022/0347516 A1 | 11/2022 | Taylor |
| 2022/0347548 A1 | 11/2022 | Watterson |
| 2022/0362613 A1 | 11/2022 | Watterson et al. |
| 2022/0362624 A1 | 11/2022 | Dalebout |
| 2022/0395729 A1 * | 12/2022 | Toth ................. G16H 40/63 |
| 2023/0039903 A1 * | 2/2023 | Brammer ............ A61B 5/0205 |
| 2023/0054845 A1 | 2/2023 | Smith |
| 2023/0122235 A1 | 4/2023 | Ashby et al. |
| 2023/0128721 A1 | 4/2023 | Plummer |
| 2023/0158358 A1 | 5/2023 | Ercanbrack et al. |
| 2023/0181993 A1 | 6/2023 | Taylor et al. |
| 2023/0191189 A1 | 6/2023 | Taylor et al. |
| 2023/0191197 A1 | 6/2023 | Ashby |
| 2023/0218975 A1 | 7/2023 | Toles et al. |
| 2023/0226401 A1 | 7/2023 | Watterson |

OTHER PUBLICATIONS

U.S. Appl. No. 17/066,485, filed Oct. 9, 2020, Weston et al.
U.S. Appl. No. 17/739,819, filed May 9, 2022, Buchanan.
U.S. Appl. No. 17/841,313, filed Jun. 15, 2022, Weston et al.
U.S. Appl. No. 17/963,822, filed Oct. 11, 2022, Powell.
U.S. Appl. No. 18/091,004, filed Dec. 29, 2022, Cox.
U.S. Appl. No. 18/103,221, filed Jan. 30, 2023, Dalebout et al.
U.S. Appl. No. 18/114,758, filed Feb. 27, 2023, Cutler et al.
U.S. Appl. No. 18/117,263, filed Mar. 3, 2023, Smith et al.
U.S. Appl. No. 18/123,026, filed Mar. 17, 2023, Silcock et al.
U.S. Appl. No. 18/132,277, filed Apr. 7, 2023, Vasquez et al.
U.S. Appl. No. 18/136,535, filed Apr. 19, 2023, Ashby et al.
U.S. Appl. No. 18/141,872, filed May 1, 2023, Ashby et al.
U.S. Appl. No. 18/205,299, filed Jun. 2, 2023, Wrobel.
U.S. Appl. No. 18/207,512, filed Jun. 8, 2023, Chuang.
U.S. Appl. No. 18/210,505, filed Jun. 15, 2023, Nielsen et al.
U.S. Appl. No. 29/702,127, filed Sep. 16, 2019, Cutler et al.
U.S. Appl. No. 62/273,852, filed Dec. 31, 2015, Watterson.
U.S. Appl. No. 63/073,081, filed Sep. 1, 2021, Ashby et al.
U.S. Appl. No. 63/079,697, filed Sep. 7, 2020, Willardson et al.
U.S. Appl. No. 63/086,793, filed Oct. 20, 2020, Ashby.
U.S. Appl. No. 63/134,036, filed Jan. 5, 2021, Ercanbrack et al.
U.S. Appl. No. 63/150,066, filed Feb. 16, 2021, Smith.
U.S. Appl. No. 63/156,801, filed Mar. 4, 2021, Watterson.
U.S. Appl. No. 63/165,498, filed Mar. 24, 2021, Archer.
U.S. Appl. No. 63/179,094, filed Apr. 23, 2021, Watterson et al.
U.S. Appl. No. 63/180,521, filed Apr. 27, 2021, Watterson et al.
U.S. Appl. No. 63/187,348, filed May 11, 2021, Dalebout et al.
U.S. Appl. No. 63/188,431, filed May 13, 2021, Plummer.
U.S. Appl. No. 63/200,903, filed Apr. 2, 2021, Watterson et al.
U.S. Appl. No. 63/211,870, filed Jun. 17, 2021, Watterson et al.
U.S. Appl. No. 63/216,313, filed Jun. 29, 2021, Watterson et al.
U.S. Appl. No. 63/229,794, filed Aug. 12, 2021, Brammer.

(56) References Cited

OTHER PUBLICATIONS

U.S. Appl. No. 63/235,002, filed Aug. 19, 2021, Smith.
U.S. Appl. No. 63/254,470, filed Oct. 11, 2021, Powell.
U.S. Appl. No. 63/278,714, filed Nov. 12, 2021, Taylor.
U.S. Appl. No. 63/289,997, filed Dec. 15, 2021, Taylor et al.
U.S. Appl. No. 63/290,455, filed Dec. 16, 2021, Taylor et al.
U.S. Appl. No. 63/290,557, filed Dec. 16, 2021, Ashby.
U.S. Appl. No. 63/298,170, filed Jan. 10, 2022, Ercanbrack et al.
U.S. Appl. No. 63/299,357, filed Jan. 13, 2022, Toles et al.
U.S. Appl. No. 63/305,976, filed Feb. 2, 2022, Watterson.
U.S. Appl. No. 63/329,270, filed Apr. 8, 2022, Vasquez et al.
U.S. Appl. No. 63/332,581, filed Apr. 25, 2022, Ashby et al.
U.S. Appl. No. 63/338,265, filed May 4, 2022, Ashby et al.
U.S. Appl. No. 63/350,072, filed Jun. 8, 2022, Chuang.
U.S. Appl. No. 63/352,539, filed Jun. 15, 2022, Nielsen et al.
U.S. Appl. No. 63/471,680, filed Jun. 7, 2023, Powell et al.

* cited by examiner

SYSTEMS AND METHODS FOR CROSS-TRAINING ON EXERCISE DEVICES

CROSS-REFERENCE TO RELATED APPLICATIONS

This application claims priority to and the benefit of U.S. Provisional Patent Application No. 63/180,458, filed on Apr. 27, 2021, which is hereby incorporated by reference in its entirety.

BACKGROUND

Background and Relevant Art

Exercise devices allow for convenient exercises and workouts without requiring large amounts of space, agreeable weather or outdoor conditions, or specialized equipment. Exercise devices can also simulate a personal trainer, custom workouts, or different locations. Unlike a personal trainer, however, exercise devices require the user to remain on the exercise device and engage with the exercise device for the duration of the workout in order to properly measure and record the user's efforts and progression.

BRIEF SUMMARY

In some embodiments, a method of compiling workout information in a workout session includes, at a workout server, receiving, via a network, first login information from a first exercise device; receiving, via the network, first workout information from the first exercise device; recording the first workout information in an active workout session; receiving, via the network, second login information from a second exercise device; receiving, via the network, second workout information from the second exercise device; and recording the second workout information in the active workout session.

This Summary is provided to introduce a selection of concepts in a simplified form that are further described below in the Detailed Description. This Summary is not intended to identify key features or essential features of the claimed subject matter.

Additional features and advantages will be set forth in the description which follows, and in part will be obvious from the description, or may be learned by the practice of the teachings herein. Features and advantages of the disclosure may be realized and obtained by means of the instruments and combinations particularly pointed out in the appended claims. Features of the present disclosure will become more fully apparent from the following description and appended claims or may be learned by the practice of the disclosure as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

The present disclosure relates generally to systems and methods for conducting a workout routine across a plurality of exercise devices. In some embodiments, each of the exercise devices includes a data connection to allow the exercise devices to communicate the presence of a uniquely identified user and associate the user with a workout routine in-progress. In some embodiments, workout routine instructions are provided by the exercise device(s) to the user. For example, the workout routine instructions may be stored on a workout server at a remote location. The workout routine instructions are transmitted to a first exercise device and presented to the user by the first exercise device while the first exercise device records workout information associated with an active workout session. The user may move to a second exercise device, which determines the user's presence, and the second exercise device may communicate with the workout server to continue presenting the workout routine instructions to the user. The second exercise device also records workout information associated with the active workout session such that workout information from both the first exercise device and the second exercise device is recorded to the workout session.

In some embodiments, the workout routine is performed ad hoc by the user. For example, the user may move between exercise devices and exercise on each of the exercise devices as the user desires. Each of the exercise devices may determine the user's presence and record workout information associated with the active workout session to a single storage location. In some embodiments, the storage location is at the workout server. In some embodiments, the storage location is on a client device local to the user. In some embodiments, the storage location is at least one of the exercise devices.

In some embodiments, a system for cross-training includes at least a first exercise device and a second exercise device that are both in data communication with a network.

The first exercise device and second exercise device communicate with a workout server over the network to receive workout routine from the workout server and to transmit workout information to the workout server. In some embodiments, the workout routine(s) are videos, text, or other video information that instructs the user to perform certain physical exercises. The workout routine may include instructions for particular physical exercises, pace, resistance settings, quantity of repetitions or quantity of sets of repetitions, or other instructions.

Figure 1:
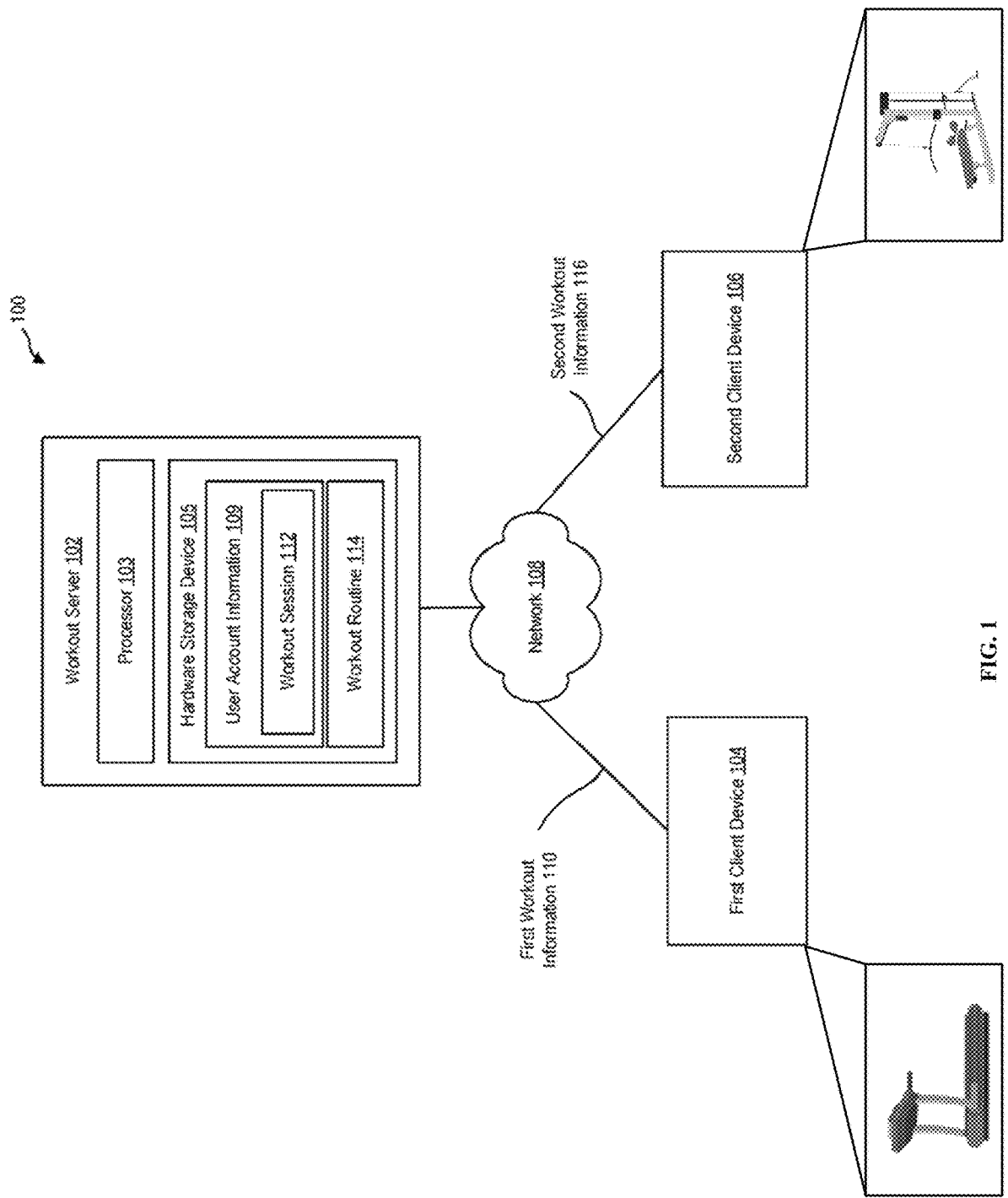
FIG. 1 is a schematic representation of a system for cross-training on multiple exercise devices, according to at least one embodiment of the present disclosure.

FIG. 1 illustrates an embodiment of a cross-training system 100 that includes a workout server 102 in communication with a first client device 104 and a second client device 106 via a network 108. The workout server 102 may store user account 109 information for a user. The user engages with the first client device 104 to perform exercises. In some embodiments, the first client device 104 is an exercise device that determines the presence of the user and transmits user login information to the workout server 102 to identify the user engaged with the first client device 104. For example, the first client device 104 may be a treadmill, exercise bicycle, resistance training exercise device, rowing device, etc. In some embodiments, the first client device 104 is an electronic device that determines the presence of the user and transmits user login information to the workout server 102 to identify the user engages with the first client device 104. For example, the first client device 104 may be a wearable electronic device, camera with image recognition, or other electronic device with sensors to measure the user's activities.

The workout server 102 includes a processor 103 and a hardware storage device 105 in data communication with the processor 103. The hardware storage device 105 may have instructions stored thereon that, when executed by the processor 103, cause the workout server 102 to perform any of the methods described herein. The workout server 102 further stores relevant information such as a user account 109 and/or workout routines 114. The first client device 104 transmits workout information 110 to the workout server 102, where the workout server 102 stores the workout information 110 in an active workout session 112 associated with the user account 109. In some embodiments, the workout server 102 includes one or more workout routines 114 that may be transmitted to the first client device 104 or other electronic device to communicate instructions to the user to perform a set of exercises. As the user performs the exercises, the first client device 104 transmits the workout information 110 to the workout server 102.

In at least one example, the workout routine 114 provides the user with instructions to perform three sets of ten repetitions of a first exercise on the first exercise device (e.g., first client device 104) followed by three sets of ten repetitions of a second exercise on the second exercise device (e.g., second client device 106). The first exercise device may determine that the user is using the first exercise device, and the first exercise device may record the user's workout information. For example, the system 100 may allow the first exercise device to communicate to the workout server 102 that the user has performed the first exercise and completed the instructed three sets of ten repetitions at a first resistance setting. The system 100 may then determine that the user has moved to the second exercise device. The second exercise device may record the user's performance of the second exercise according to the instructions and, subsequently or concurrently, report the workout information to the workout server 102.

In some embodiments, the workout routine 114 includes video or audio information to entertain the user during the workout. For example, the workout routine 114 may include video information and/or audio information experienced by the user during the workout, such as scenery, encouragement or music, information of what muscle groups the exercise focuses upon or how the exercises complement one another, or combinations thereof. In some examples, the workout routine 114 may display a moving viewpoint of a beach or road during a run or bicycle ride workout routine. In some examples, the workout routine 114 may display a representative user performing the exercise to ensure proper form during strength training workout routines.

The workout routine 114 may include audio information to the user. In some embodiments, the audio information provides the workout routine instructions to the user. In some embodiments, the audio information is music, such as music with a tempo or beats-per-minute (BPM) that assists the user in maintain a particular cadence, such as when riding a bicycle. In some embodiments, the audio information includes verbal encouragement from a trainer. In some embodiments, the audio information includes verbal instructions on proper form for performing the exercise.

In some embodiments, the user prefers to exercise without explicit instructions or a particular routine. The user may initiate a workout session 112 from a first client device 104 or exercise device and the first client device 104 or exercise device may communicate with a workout server 102 to report first workout information 110 to the workout server 102. Any additional exercise devices (e.g., second client device 106) that determine that the user is present and using the exercise device may communicate second workout information 116 to the workout server 102 to add to the active workout session 112.

For example, the user may initiate a workout session on a treadmill and run for 20 minutes at 8 miles per hour. The treadmill can, during the workout session or after the workout session, communicate that workout information to a workout server. The user may, subsequently, move to a resistance training machine for strength training exercises. The resistance training machine may determine the user's presence on the resistance training machine and record additional workout information. For example, the resistance training machine may record the user performing a first set of bench press exercises at 150 pounds for 10 repetitions, a second set at 140 pounds for 8 repetitions, and a third set at 130 pounds for 6 repetitions. The resistance training machine may transmit that additional workout information including the bench press information to the workout server, where the workout server compiles the run information and the bench press information into a single workout session, despite the information originating from different exercise devices.

The user may continue to perform strength training exercises on the resistance training machine and adding to the workout information of the workout session. For example, the user may perform overhead presses and preacher curls, and the resistance training machine may record the user's performance and transmit the workout information to the workout server. In some examples, the user may then return to the treadmill to cooldown and finish their workout.

In some embodiments, the exercise devices are in data communication with a health and fitness platform that tracks and/or analyzes user workout information. Examples include the iFit platform from ICON Health and Fitness. The workout server 102 receives the workout information from the exercise devices and stores the workout information 110, 116. In some embodiments, once a user begins a workout routine, any additional workout information received is added to the active workout session 112. In some embodiments, the active workout session 112 is closed and/or finalized when the workout routine instructions are completed by the user. For example, the active workout session is closed and/or finalized when the user completed a guided cross-training session on a treadmill and a rowing machine based on a workout routine received from the workout server 102.

In some embodiments, the active workout session 112 will continue compiling workout information until the workout session 112 is closed and/or finalized by the user. For example, the user may complete a guided bicycle ride on a stationary bicycle based on a workout routine received from the workout server, and then the user may change to a second exercise device (such as a resistance training machine) to perform additional strength training exercises selected by the user independent of a predetermined workout routine. Those additional strength training exercises may be recorded by the second exercise device and transmitted to the workout server to be compiled in the active workout session with the completed bicycle workout routine. The user may then close and/or finalize the workout session.

In the event the user forgets or chooses not to close and/or finalize the workout session 112, some embodiments according to the present disclosure include a timeout condition to close and/or finalize the workout session 112. For example, if the active workout session is not closed and/or finalized at the completion of a predetermined workout routine instruction or the user does not close and/or finalize the workout session through explicit input or command, the workout server may close and/or finalize the active workout session after not receiving additional workout information for a predetermined period of time. In some embodiments, the workout server 102 may have a timeout condition of 2 hours or less. In some embodiments, the workout server 102 may have a timeout condition of 1 hour or less. In some embodiments, the workout server 102 may have a timeout condition of 30 minutes or less. In some embodiments, the workout server 102 may have a timeout condition of 15 minutes or less. A timer used for the timeout condition may be reset based on receiving workout information from a sensor or exercise device.

In some embodiments, the timer is reset upon receiving login information or other detection of a user present on an exercise device. For example, a user may complete a first exercise on a first exercise device and leave the first exercise device to change to a second exercise device. If the time condition is 15 minutes, the workout session may timeout before the workout server receives workout information from the second exercise device. The timer used for the timeout condition may be reset upon the second exercise device determining the user is present on/at the second exercise device to allow the user time to complete the desired exercise. For example, if the second exercise device transmits workout information upon completion of the exercise, a cardio exercise that requires 30 minutes would always cause a 30 minute timeout condition to expire unless the timer resets upon the second exercise device transmitting the user presence information.

Systems including exercise devices according to the present disclosure may include one or more sensors to collect workout information. In some embodiments, the first exercise device includes sensors to communicate workout information including duration of the workout, running speed, cycling speed, cadence, power output (Watts), weight of resistance, quantity of repetitions, rate of repetitions, range of motion, user weight, user height, user heartrate, other workout information, or combinations thereof. The sensors may communicate the workout information to the workout server directly (such as via a dedicated communication device associated with or integrated in the sensor), or the sensor(s) may communicate the workout information to a computing device of the first exercise device which, in turn, communicates the workout information to the workout server.

In some embodiments, the sensor(s) of the exercise device communicate the workout information to a workout server, and the workout service compiles the workout information with second workout information from sensor(s) of a second exercise device. In some embodiments, the second exercise device includes sensors to communicate workout information including duration of the workout, running speed, cycling speed, cadence, power output (Watts), weight of resistance, quantity of repetitions, rate of repetitions, range of motion, user weight, user height, user heartrate, other workout information, or combinations thereof. The sensors may communicate the workout information to the workout server directly (such as via a dedicated communication device associated with or integrated in the sensor), or the sensor(s) may communicate the workout information to a computing device of the second exercise device which, in turn, communicates the workout information to the workout server.

The workout information is communicated to the workout server via a network. In some embodiments, the network is the Internet or World Wide Web. In some embodiments, the network is a wide area network (WAN) or a local area network (LAN). For example, the network may communicate workout information between the exercise device(s) and the workout server at a remote location through one or more network nodes. In other examples, the workout server may be local to the exercise device(s), and the workout information is communicated to the workout server via a LAN.

The workout server is a computing device that receives and/or stores workout information in respective workout sessions associated with a user account. In some embodiments, the workout server stores the workout information at the workout server. In some embodiments, the workout server compiles the information and/or analyzes the workout information, and the workout server sends at least a portion of the workout information or a summary of the workout session to a client personal device or to exercise device(s) for viewing. In an example, the workout server generates a workout session report with at least some of the workout information and sends the workout session report to the user for viewing on a client device. The workout session report may be stored at the workout server.

The user account is associated with the user at the workout server, and the user may access the user account to upload workout information from a current workout session, view workout information, download workout information, analyze workout information, or combinations thereof. In some embodiments, the user account is associated with the user for a plurality of exercise devices and/or types of workouts. For example, the user account may allow a user to use a single profile to track workout information across aerobic workouts, strength training, flexibility, cross-training, or other workout types. In some embodiments, a single profile can allow the user to use a single login that is consistent across exercise devices and/or client devices.

In some embodiments, the user account is associated with a database of workout information, workout sessions, workout routines, workout preferences, or combinations thereof that are available to the exercise system to provide user-specific information and recommendations. In some examples, the workout information, workout sessions, workout routines, and workout preferences are determined from the user's history of completed exercises and workouts. In some examples, the workout information, workout sessions, workout routines, and workout preferences are received from direct user inputs, such as selecting particular preferences from a predetermined set of options or user selections of workout routines to add to a queue of future workouts to complete. In at least one example, the user account includes a list of exercise devices available to the user. The system may present to the user workout routines or suggestions that are available to the user based on the exercise devices available to the user. For example, the user account may indicate that the user has an exercise bicycle, a treadmill, a rowing machine, and a resistance training machine, and the system may provide to the user workout routines that include exercises on one or more of the available exercise devices.

The user account may be associated with workout information, workout sessions, workout routines, workout preferences, or combinations thereof stored on the workout server. In some embodiments, the user account is associated with workout information, workout sessions, workout routines, workout preferences, or combinations thereof stored on a client personal device. A client personal device may be any electronic device that is local to the user and/or to the exercise device that is not the exercise device itself. For example, the client personal device may be a smartphone, tablet computer, hybrid computer, laptop computer, wearable electronic device, or other electronic device with data connectivity. In some embodiments, the user account is associated with workout information, workout sessions, workout routines, workout preferences, or combinations thereof stored on a client exercise device.

In some embodiments, at least a portion of the workout information, workout sessions, workout routines, workout preferences, or combinations thereof are stored on the workout server and accessible by a client personal device or client exercise device. For example, the client device(s) may access the workout information, workout sessions, workout routines, workout preferences, or combinations thereof stored on the workout server for display or other communication of the workout information, workout sessions, workout routines, workout preferences, or combinations thereof to the user. In at least one example, the client device(s) may access the workout information, workout sessions, workout routines, workout preferences, or combinations thereof stored on the workout server and combine or compile the workout information, workout sessions, workout routines, workout preferences, or combinations thereof stored on the workout server with the one or more of workout information, workout sessions, workout routines, workout preferences, or combinations thereof stored on the client device(s). For example, the client personal device may record heartrate workout information and access workout information of the workout session to combine the heartrate workout information with other workout information from the workout server. The client personal device may then display the combined results of the workout session or upload the combined results to the workout server.

In some embodiments, at least a portion of the workout information, workout sessions, workout routines, workout preferences, or combinations thereof are stored on a client device and accessible by the workout server. For example, the user may decide to run two miles (3.2 kilometers) before using a resistance training exercise device to perform a strength training workout routine. The user may carry on their person the personal client device (such as a smartphone or wearable device) during the run, and the personal client device may record workout information regarding the run while the user is away from the resistance training exercise device. When the user approaches the resistance training exercise device, in some embodiments, the resistance training exercise device may determine the user is present and communicate with the workout server.

Figure 2:
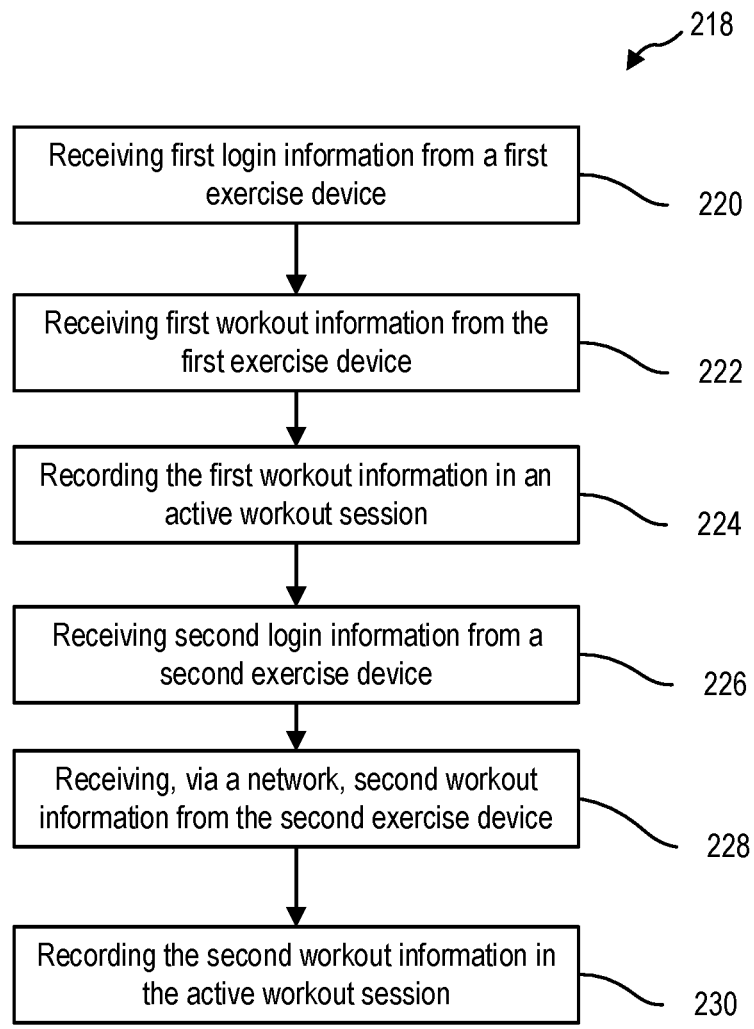
FIG. 2 is a flowchart illustrating a method for cross-training on multiple exercise devices, according to at least one embodiment of the present disclosure.

FIG. 2 is a flowchart illustrating an embodiment of a method 218 of recording a cross-training workout session at a workout server (e.g., workout server 102 of FIG. 1). In some embodiments, the method 218 includes receiving first login information from a first exercise device at 220. The first login information from the first exercise device identifies the user account associated with the user engaged with the first exercise device. The method 218 further includes receiving first workout information from the first exercise device at 222 and recording the first workout information in an active workout session at 224. In some embodiments, the workout information and/or workout session is stored locally at the workout server. In some embodiments, the workout information and/or workout session is transmitted to a remote storage device by the workout server.

The method 218 further includes receiving second login information from a second exercise device at 226. The first login information from the first exercise device identifies the user account associated with the user engaged with the first exercise device. When the second login information identifies the user engaged with the second exercise device is the same user as that associated with the first login information, the method 218 further includes receiving second workout information from the second exercise device at 228 and recording the first workout information in an active workout session at 230.

In some embodiments, the workout server may receive workout information from the client personal device regarding a first portion of a workout session and from the resistance training exercise device regarding a second portion of the workout session. For example, the workout server may access the workout information collected by the client personal device to add the workout information of the run to any workout information collected by the resistance training exercise device during the selected strength training workout routine. In some embodiments, the workout server may receive workout information concurrently from both the client personal device and the resistance training exercise device regarding the workout session. While the user is performing the strength training workout routine, one or more sensors of the resistance training exercise device may collect workout information regarding repetitions, form, cadence, weight, range of motion, etc. while the client personal device measures the user's heartrate. The workout server may receive workout information concurrently from both the client personal device and the resistance training exercise device regarding the workout session.

In another example, a first exercise device may include internet connectivity to the workout server through a communication device integrated into the first exercise device and the second exercise device may include a local data connection device that allows the second exercise device to communicate with a client personal device. In some embodiments, the client personal device subsequently communicates the workout information collected by the second exercise device to the workout server.

Centralizing the workout information for one or more workout sessions at a workout server can allow for additional benefits, such as using machine learning models to customize future workout routines or recommendations based on the workout information stored on or accessed by the workout server. In some embodiments, the workout server is a general-purpose computer, and the workout server or other computing device connected to the workout server allows modularity and/or additional functionality beyond the processing resources and/or available software on the workout server. For example, the workout server, even when a general-purpose computer, may be updated at different cycles than the processing hardware of the exercise device. In at least one example, the workout server or other computing device is configured to execute at least one machine learning (ML) model to analyze and refine the ML model based upon the workout information and/or user inputs received by the ML model.

As illustrated in the foregoing discussion, the present disclosure utilizes a variety of terms to describe features and advantages of the machine learning model. As used herein, a "machine learning model" refers to a computer algorithm or model (e.g., a classification model, a regression model, a language model, an object detection model) that can be tuned (e.g., trained) based on training input to approximate unknown functions. For example, a machine learning model may refer to a neural network or other machine learning algorithm or architecture that learns and approximates complex functions and generate outputs based on a plurality of inputs provided to the machine learning model. In some embodiments, a machine learning system, model, or neural network described herein is an artificial neural network. In some embodiments, a machine learning system, model, or neural network described herein is a convolutional neural network.

In some embodiments, a machine learning system, model, or neural network described herein is a recurrent neural network. In at least one embodiment, a machine learning system, model, or neural network described herein is a Bayes classifier. As used herein, a "machine learning system" may refer to one or multiple machine learning models that cooperatively generate one or more outputs based on corresponding inputs. For example, a machine learning system may refer to any system architecture having multiple discrete machine learning components that consider different kinds of information or inputs. In some embodiments, the ML model may allow for recommendations of workout routines, changes to repetitions, changes to weights or resistances, exercise duration or intensity, or for other changes based upon the user's workout information and/or aggregated workout information from a plurality of users. A ML model may consider the plurality of exercise devices to which the user has access, as indicated by the user account information. The ML model may suggest workout routines that include exercises using multiple exercise devices, either by predetermined workout routines or workout routines generated through the ML model.

In some embodiments, a method of compiling workout information for a workout session includes, at a workout server, receiving first login information from a first exercise device. The first login information may be provided to the first exercise device and subsequently received by the workout server in one or more ways.

Figure 3:
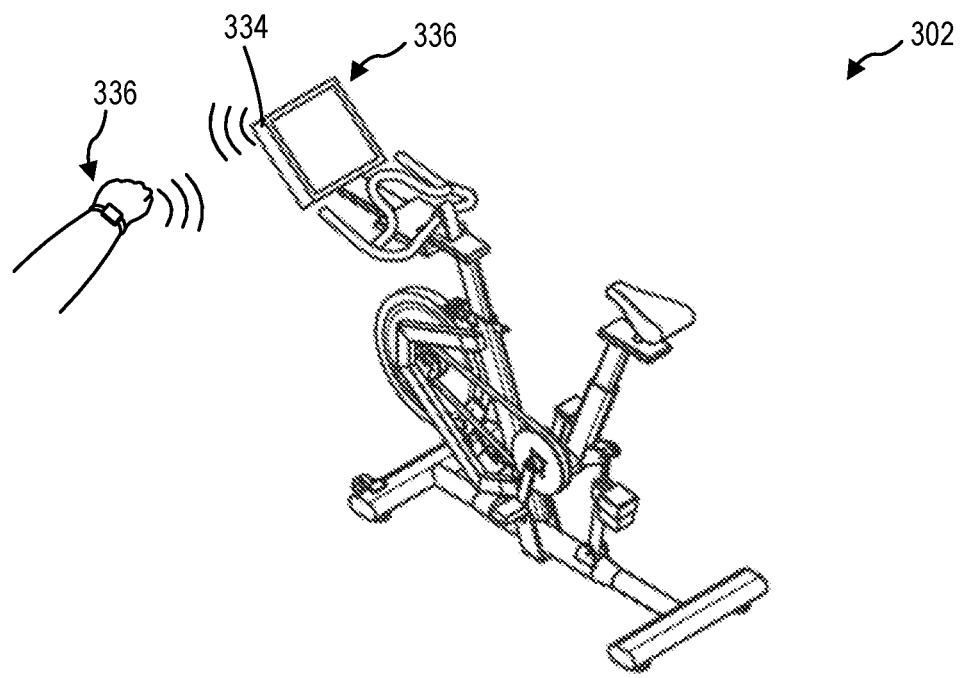
FIG. 3 is a perspective view of part of a system for cross-training on multiple exercise devices with electromagnetic user detection, according to at least one embodiment of the present disclosure.

For example, receiving the first login information from the first exercise device may include the first exercise device receiving near-field communication (NFC) login information from a user, as shown in FIG. 3. In some embodiments, the NFC login information is received from an NFC user device 332 that is uniquely associated with the user's account. For example, the NFC user device 332 may be a key fob, a smartphone or other computing device such as a smartwatch, a wristband, a ring, or incorporated into an article of clothing or exercise equipment, such as the user's shoes, shirt, shorts, tights, or other article of clothing. The NFC user device 332 may be brought into NFC range with a transceiver 334 of the first exercise device 302, and the first exercise device 302 may detect the presence of the NFC user device 332 to uniquely identify the user. A computing device 336 of the first exercise device 302 may then transmit the user account information to the workout server to associate the user of the first exercise device 302 with a workout session.

In another example, receiving the first login information from the first exercise device may include the first exercise device receiving electromagnetic login information, such as radio-frequency identification (RFID) login information, from a user. In some embodiments, the RFID login information is received from a RFID user device that is uniquely associated with the user's account. For example, the RFID user device may be a key fob, a smartphone, or other computing device such as a smartwatch, a wristband, a ring, or incorporated into an article of clothing or exercise equipment, such as the user's shoes, shirt, shorts, tights, or other article of clothing. The RFID user device may be brought into RFID range with a transceiver of the first exercise device, and the first exercise device may detect the presence of the RFID user device to uniquely identify the user. The first exercise device may then transmit the user account information to the workout server to associate the user of the first exercise device with a workout session.

Figure 4:
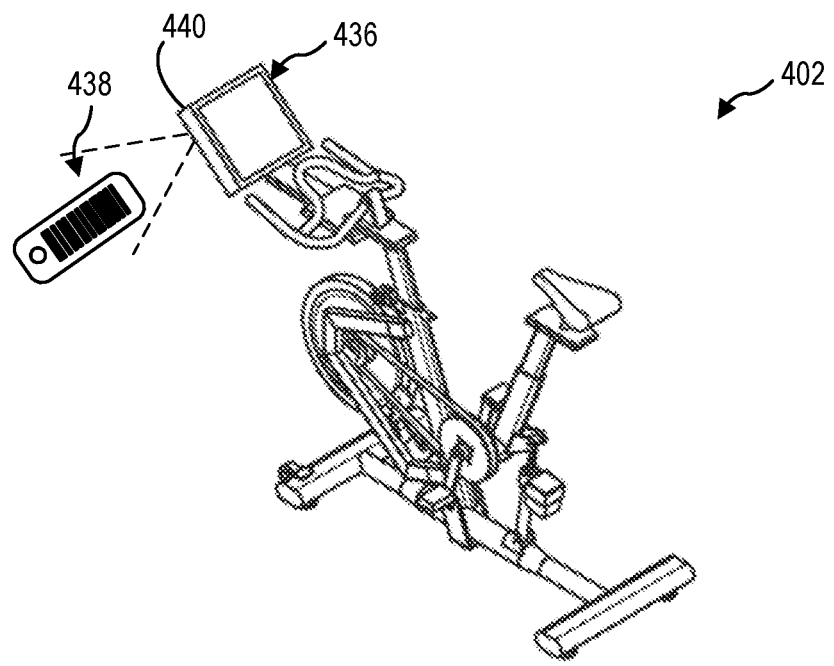
FIG. 4 is a perspective view of part of a system for cross-training on multiple exercise devices with machine-readable user detection, according to at least one embodiment of the present disclosure.

In some examples, such as illustrated in FIG. 4, receiving the first login information from the first exercise device may include the first exercise device reading a barcode 438, QR code, or other machine-readable binary image code provided by a user. In some embodiments, the barcode login information is received from a user barcode 438 that is uniquely associated with the user's account. For example, the user barcode 438 may be printed on, displayed by, or integrated into a key fob, a smartphone or other computing device such as a smartwatch, a wristband, a ring, or incorporated into an article of clothing or exercise equipment, such as the user's shoes, shirt, shorts, tights, or other article of clothing. The user barcode 438 may be brought into range of a camera 440 or other image capture device of the first exercise device 402, and the first exercise device 402 may detect the presence of the user barcode 438 to uniquely identify the user. A computing device 436 of the first exercise device 402 may then transmit the user account information to the workout server to associate the user of the first exercise device with a workout session.

Figure 5:
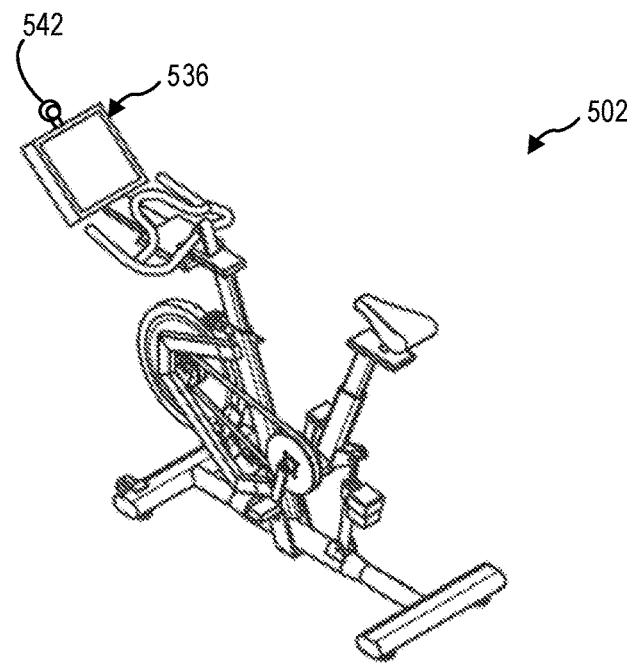
FIG. 5 is a perspective view of part of a system for cross-training on multiple exercise devices with biometric user detection, according to at least one embodiment of the present disclosure.

In some embodiments, such as the embodiment illustrated in FIG. 5, receiving the first login information from the first exercise device 502 may include the first exercise device 502 receiving biometric information (e.g., biometric login information) from a user. In some embodiments, the biometric information is received from the user's body and is uniquely associated with the user's account. For example, receiving the biometric information may include fingerprint recognition, facial recognition, ocular recognition (including iris or ocular capillary recognition), palm recognition, voice recognition, or other biometric information methods. The user may place a portion of their body in contact with or near a biometric identification device (e.g., fingerprint scanner or video camera 542 for facial recognition), and the first exercise device 502 may detect the presence of the user to collect the biometric information and uniquely identify the user. A computing device 536 of the first exercise device 502 may then transmit the user account information to the workout server to associate the user of the first exercise device with a workout session.

Figure 6:
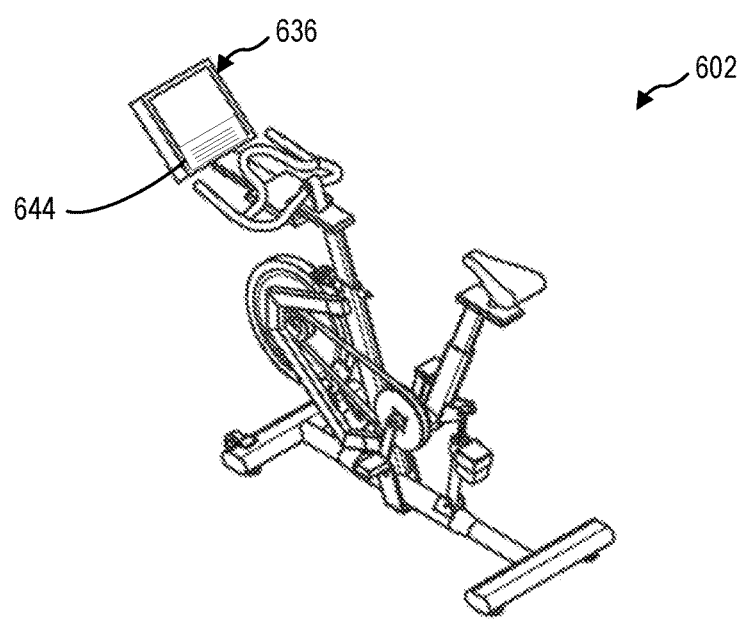
FIG. 6 is a perspective view of part of a system for cross-training on multiple exercise devices with human interface device user detection, according to at least one embodiment of the present disclosure.

In some examples, receiving the first login information from the first exercise device may include the first exercise device receiving user login information from a conventional human interface device (HID) to login to the first exercise device. In the embodiment illustrated in FIG. 6, the user login information is provided by user input to the HID 644, and the user login information is uniquely associated with the user's account. For example, the HID 644 may be a keyboard, a number pad, a voice recognition device, a touchscreen or other touch-sensitive device, a mouse, a trackball, or another HID that allows the user to input the user login information. After receiving the user login information from the HID 644, a computing device 636 of the first exercise device 602 may then transmit the user account information to the workout server to associate the user of the first exercise device with a workout session.

Figure 7:
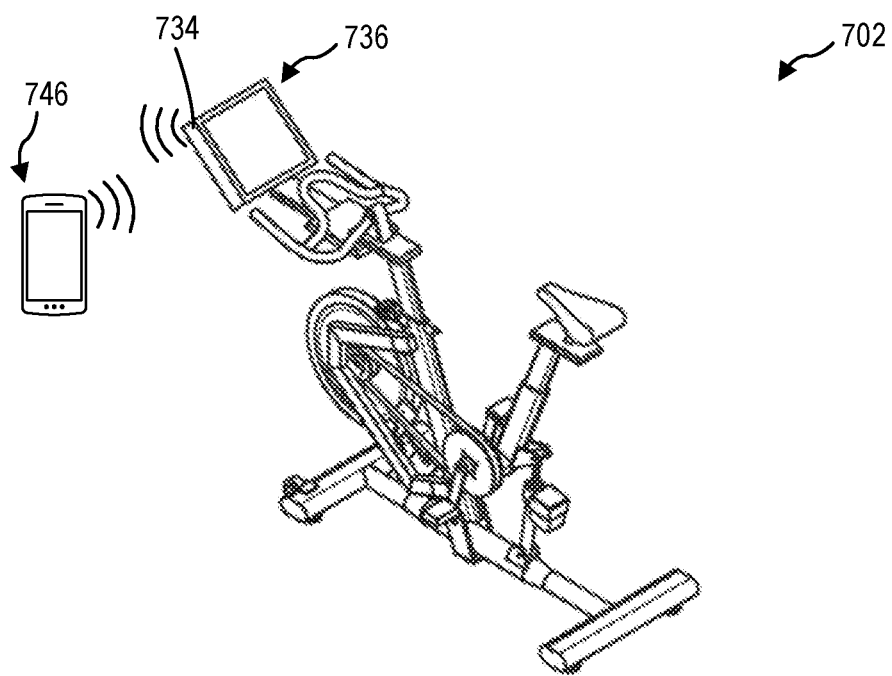
FIG. 7 is a perspective view of part of a system for cross-training on multiple exercise devices with paired client device user detection, according to at least one embodiment of the present disclosure.

In some embodiments, the user login information is received from a data communication with a paired client device that is uniquely associated with the user's account, such as shown in FIG. 7. For example, the paired client device 746 may be a key fob, a smartphone or other computing device such as a smartwatch, a wristband, a ring, or incorporated into an article of clothing or exercise equipment, such as the user's shoes, shirt, shorts, tights, or other article of clothing. The paired client device may be brought into communication range with a transceiver 734 of the first exercise device 702, and the first exercise device 702 may detect the presence of the paired client device 746 to uniquely identify the user. A computing device 736 of the first exercise device 702 may then transmit the user account information to the workout server to associate the user of the first exercise device 702 with a workout session.

In some embodiments, the paired client device 746 communicates with the first exercise device 702 using a wireless data communication protocol. For example, the client device 746 and the first exercise device 702 may communicate through a Bluetooth data connection. In some examples, the client device 746 and the first exercise device 702 may communicate through a Wi-Fi direct data connection. In some examples, the client device 746 and the first exercise device 702 may communicate through a proprietary data connection protocol.

In some examples, receiving the first login information from the first exercise device may include the first exercise device receiving a selection by a user of a saved user account from one or more user accounts saved locally on the first exercise device. In some embodiments, the selected saved user account is uniquely associated with the user's account. For example, the first exercise device may have a plurality of saved user accounts that represent each member of a family in a household. The plurality of saved user accounts may be saved locally on the first exercise device. The first exercise device may present to the user a list of available saved user accounts, and the user may select (such as by a touchscreen or other HID) the saved user account associated with the user. The first exercise device may then transmit the user account information to the workout server to associate the user of the first exercise device with a workout session.

In some embodiments, the user subsequently begins a workout by engaging with the first exercise device. In some embodiments, the user may browse or search for a predetermined workout routine, which the first exercise device or other device may then present to the user. The method further includes receiving first workout information from the first exercise device. In some embodiments, the first exercise device measures the workout information of the user engaged with the first exercise device.

In some embodiments, the first exercise device receives the workout information of the user engaged with the first exercise device from a wearable device or other electronic device that measures the workout information and relays the workout information to the first exercise device. The first exercise device may include sensors to record and/or communicate workout information including duration of the workout, running speed, cycling speed, cadence, power output (Watts), weight of resistance, quantity of repetitions, rate of repetitions, range of motion, user weight, user height, user heartrate, other workout information, or combinations thereof. The sensors of the first exercise device may communicate the workout information to the workout server directly (such as via a dedicated communication device associated with or integrated in the sensor), or the sensor(s) may communicate the workout information to a computing device of the first exercise device which, in turn, communicates the workout information to the workout server.

Upon receiving the first workout information from the first exercise device, the workout server assigns the first workout information to a workout session associated with the user account. The active workout session may include any workout information associated with the user account that is received by the workout server. In some embodiments, the active workout session remains active for a predetermined period of time since the last workout information was received or until a closure instruction is received from an exercise device. For example, the workout session may remain active based on a timeout condition that is based upon when the last workout information was received. In some embodiments, the workout session will close upon receiving a termination instruction from the exercise device. For example, the user may select an option on the exercise device to terminate the workout session, and the exercise device transmits the termination instruction to the workout server. The workout server may then terminate the workout session, disallowing any further workout information to be added to the workout session. In some examples, the termination instruction may terminate a workout session irrespective of a timeout condition.

In some embodiments, the workout server may have a timeout condition of 2 hours or less. In some embodiments, the workout server may have a timeout condition of 1 hour or less. In some embodiments, the workout server may have a timeout condition of 30 minutes or less. In some embodiments, the workout server may have a timeout condition of 15 minutes or less. A timer used for the timeout condition may be reset based on receiving workout information from a sensor or exercise device.

In some embodiments, the timer is reset upon receiving login information or other detection of a user present on an exercise device. For example, a user may complete a first exercise on a first exercise device and leave the first exercise device to change to a second exercise device. If the time condition is 15 minutes, the workout session may timeout before workout server receives workout information from the second exercise device. The timer used for the timeout condition may be reset upon the second exercise device determining the user is present on/at the second exercise device to allow the user time to complete the desired exercise. For example, if the second exercise device transmits workout information upon completion of the exercise, a cardio exercise that requires 30 minutes would always cause a 30-minute timeout condition to expire unless the timer resets upon the second exercise device transmitting the user presence information.

The method further includes receiving second login information from a second exercise device. In at least one embodiment, the second login information is received from the second exercise device within a timeout condition. In some embodiments, the second login information is received before a termination instruction is received at the workout server. The second login information from the second exercise device is login information that is associated with the same user account as the first login information, but the second login information may be collected by the second exercise device in the same or different manner than the first login information is collected by the first exercise device. For example, the first login information may be provided by the user to the first exercise device via an NFC user device, and the second login information may be provided by the user to the second exercise device via a QR code. In another example, the first login information may be provided by the user to the first exercise device by selecting a locally saved user account, and the second login information may be provided by the user to the second exercise device by selecting a locally saved user account. In another example, the first login information may be provided by the user to the first exercise device by a paired client device, and the second login information may be provided by the user to the second exercise device by the paired client device.

Receiving the second login information from the first exercise device may include the second exercise device receiving NFC login information from a user. In some embodiments, the NFC login information is received from an NFC user device that is uniquely associated with the user's account. For example, the NFC user device may be a key fob, a smartphone or other computing device such as a smartwatch, a wristband, a ring, or incorporated into an article of clothing or exercise equipment, such as the user's shoes, shirt, shorts, tights, or other article of clothing. The NFC user device may be brought into NFC range with a transceiver of the second exercise device, and the second exercise device may detect the presence of the NFC user device to uniquely identify the user. The second exercise device may then transmit the user account information to the workout server to associate the user of the second exercise device with the workout session.

In some examples, receiving the second login information from the second exercise device may include the second exercise device reading a barcode, QR code, or other machine-readable binary image code provided by a user. In some embodiments, the barcode login information is received from a user barcode that is uniquely associated with the user's account. For example, the user barcode may be printed on, displayed by, or integrated into a key fob, a smartphone or other computing device such as a smartwatch, a wristband, a ring, or incorporated into an article of clothing or exercise equipment, such as the user's shoes, shirt, shorts, tights, or other article of clothing. The user barcode may be brought into range of a camera or other image capture device of the second exercise device, and the second exercise device may detect the presence of the user barcode to uniquely identify the user. The second exercise device may then transmit the user account information to the workout server to associate the user of the second exercise device with the workout session.

For example, receiving the first login information from the second exercise device may include the second exercise device receiving RFID login information from a user. In some embodiments, the RFID login information is received from a RFID user device that is uniquely associated with the user's account. For example, the RFID user device may be a key fob, a smartphone or other computing device such as a smartwatch, a wristband, a ring, or incorporated into an article of clothing or exercise equipment, such as the user's shoes, shirt, shorts, tights, or other article of clothing. The RFID user device may be brought into RFID range with a transceiver of the second exercise device, and the second exercise device may detect the presence of the RFID user device to uniquely identify the user. The second exercise device may then transmit the user account information to the workout server to associate the user of the second exercise device with the active workout session.

In some examples, receiving the second login information from the second exercise device may include the second exercise device receiving biometric information from a user. In some embodiments, the biometric information is received from the user's body and is uniquely associated with the user's account. For example, receiving the biometric information may include fingerprint recognition, facial recognition, ocular recognition (including iris or ocular capillary recognition), palm recognition, voice recognition, or other biometric information methods. The user may place a portion of their body in contact with or near a biometric identification device (e.g., fingerprint scanner or video camera for facial recognition), and the second exercise device may detect the presence of the user to collect the biometric information and uniquely identify the user. The second exercise device may then transmit the user account information to the workout server to associate the user of the second exercise device with a workout session.

In some examples, receiving the second login information from the second exercise device may include the second exercise device receiving user login information from a conventional HID to login to the second exercise device. In some embodiments, the user login information is provided by user input to the HID device, and the user login information is uniquely associated with the user's account. For example, the HID device may be a keyboard, a number pad, a voice recognition device, a touchscreen or other touch-sensitive device, a mouse, a trackball, or other HID devices that allow the user to input the user login information. After receiving the user login information from the HID, the second exercise device may then transmit the user account information to the workout server to associate the user of the second exercise device with the workout session.

In some embodiments, the user login information is received from a data communication with a paired client device that is uniquely associated with the user's account. For example, the paired client device may be a key fob, a smartphone or other computing device such as a smartwatch, a wristband, a ring, or incorporated into an article of clothing or exercise equipment, such as the user's shoes, shirt, shorts, tights, or other article of clothing. The paired client device may be brought into communication range with a transceiver of the second exercise device, and the second exercise device may detect the presence of the paired client device to uniquely identify the user. The second exercise device may then transmit the user account information to the workout server to associate the user of the second exercise device with a workout session.

In some embodiments, the paired client device communicates with the second exercise device using a wireless data communication protocol. For example, the client device and the second exercise device may communicate through a Bluetooth data connection. In some examples, the client device and the second exercise device may communicate through a Wi-Fi direct data connection. In some examples, the client device and the second exercise device may communicate through a proprietary data connection protocol.

In some examples, receiving the second login information from the second exercise device may include the second exercise device receiving a selection by a user of a saved user account from one or more user accounts saved locally on the second exercise device. In some embodiments, the selected saved user account is uniquely associated with the user's account. For example, the second exercise device may have a plurality of saved user accounts that represent each member of a family in a household. The plurality of saved user accounts may be saved locally on the second exercise device. The second exercise device may present to the user a list of available saved user accounts, and the user may select (such as by a touchscreen or other HID) the saved user account associated with the user. The second exercise device may then transmit the user account information to the workout server to associate the user of the second exercise device with a workout session.

The method further includes receiving, at the workout server, second workout information from the second exercise device. In some embodiments, the second exercise device measures the second workout information of the user engaged with the second exercise device.

In some embodiments, the second exercise device receives the workout information of the user engaged with the second exercise device from a wearable device or other electronic device that measures the workout information and relays the workout information to the second exercise device. The second exercise device may include sensors to record and/or communicate workout information including duration of the workout, running speed, cycling speed, cadence, power output (Watts), weight of resistance, quantity of repetitions, rate of repetitions, range of motion, user weight, user height, user heartrate, other workout information, or combinations thereof. The sensors of the second exercise device may communicate the second workout information to the workout server directly (such as via a dedicated communication device associated with or integrated in the sensor), or the sensor(s) may communicate the second workout information to a computing device of the second exercise device which, in turn, communicates the second workout information to the workout server. Upon receiving the second workout information from the second exercise device, the workout server assigns the second workout information to the active workout session associated with the user account.

In at least one embodiment, the method further includes terminating the active workout session. The active workout session may be terminated by expiration of a timeout condition, by completion of a selected workout routine, or by receipt of a termination instruction from an exercise device. In at least one example, the workout session remains active after completing a workout routine, as the user may desire to select an addition workout routine or continue the workout session with ad hoc exercises.

Workout information from the workout session may be presented to the user and/or recorded for later viewing or analysis. For example, the workout information for the workout session may be presented to the user on a display of the most recently used exercise device, via a web portal, via a native application on a client device, or through another presentation mechanism. The user may then be able to better understand his or her fitness, progression, or goals. The workout information may be input into a ML model to better suggest or adapt workout routines for the user. By allowing a user to transition between multiple exercise devices within a single active workout session, a workout system can provide a user a more complete workout with greater variety to ensure an effective, efficient, and enjoyable workout.

INDUSTRIAL APPLICABILITY

The present disclosure relates generally to systems and methods for conducting a workout routine across a plurality of exercise devices. In some embodiments, each of the exercise devices includes a data connection to allow the exercise devices to communicate the presence of a uniquely identified user and associate the user with a workout routine in-progress. In some embodiments, workout routine instructions are provided by the exercise device(s) to the user. For example, the workout routine instructions may be stored on a workout server at a remote location. The workout routine instructions are transmitted to a first exercise device and presented to the user by the first exercise device while the first exercise device records workout information associated with an active workout session. The user may move to a second exercise device, which determines the user's presence, and the second exercise device may communicate with the workout server to continue presenting the workout routine instructions to the user. The second exercise device also records workout information associated with the active workout session such that workout information from both the first exercise device and the second exercise device is recorded to the workout session.

In some embodiments, the workout routine is performed ad hoc by the user. For example, the user may move between exercise devices and exercise on each of the exercise devices as the user desires. Each of the exercise devices may determine the user's presence and record workout information associated with the active workout session to a single storage location. In some embodiments, the storage location is at the workout server. In some embodiments, the storage location is on a client device local to the user. In some embodiments, the storage location is at least one of the exercise devices.

In some embodiments, a system for cross-training includes at least a first exercise device and a second exercise device that are both in data communication with a network. The first exercise device and second exercise device communicate with a workout server over the network to receive workout routine from the workout server and to transmit workout information to the workout server. In some embodiments, the workout routine(s) are videos, text, or other video information that instructs the user to perform certain physical exercises. The workout routine may include instructions for particular physical exercises, pace, resistance settings, quantity of repetitions or quantity of sets of repetitions, or other instructions.

In at least one example, the workout routine provides the user with instructions to perform three sets of ten repetitions of a first exercise on the first exercise device followed by three sets of ten repetitions of a second exercise on the second exercise device. The first exercise device may determine that the user is using the first exercise device, and the first exercise device may record the user's performance. For example, the system may allow the first exercise device to communicate to the workout server that the user has performed the first exercise and completed the instructed three sets of ten repetitions at a first resistance setting. The system may then determine that the user has moved to the second exercise device. The second exercise device may record the user's performance of the second exercise according to the instructions and, subsequently or concurrently, report the workout information to the workout server.

In some embodiments, the workout routine includes video or audio information to entertain the user during the workout. For example, the workout routine may include video information and/or audio information experienced by the user during the workout, such as scenery, encouragement or music, information of what muscle groups the exercise focuses upon or how the exercises complement one another, or combinations thereof. In some examples, the workout routine may display a moving viewpoint of a beach or road during a run or bicycle ride workout routine. In some examples, the workout routine may display a representative user performing the exercise to ensure proper form during strength training workout routines.

The workout routine may include audio instructions to the user. In some embodiments, the audio instructions provide the workout routine instructions to the user. In some embodiments, the audio information is music, such as music with a tempo or beats-per-minute (BPM) that assists the user in maintaining a particular cadence, such as when riding a bicycle. In some embodiments, the audio information includes verbal encouragement from a trainer. In some embodiments, the audio information includes verbal instructions on proper form for performing the exercise.

In some embodiments, the user prefers to exercise without explicit instructions or a particular routine. The user may initiate a workout session from a client device or exercise device and the client device or exercise device may communicate with a workout server to report workout information to the workout server. Any additional exercise devices that determine that the user is present and using the exercise device may communicate additional workout information to the workout server to add to the active workout session.

For example, the user may initiate a workout session on a treadmill and run for 20 minutes at 8 miles per hour. The treadmill can, during the workout session or after the workout session, communicate that workout information to a workout server. The user may, subsequently, move to a resistance training machine for strength training exercises. The resistance training machine may determine the user's presence on the resistance training machine and record additional workout information. For example, the resistance training machine may record the user performing a first set of bench press exercises at 150 pounds for 10 repetitions, a second set at 140 pounds for 8 repetitions, and a third set at 130 pounds for 6 repetitions. The resistance training machine may transmit that additional workout information including the bench press information to the workout server, where the workout server compiles the run information and the bench press information into a single workout session, despite the information originating from different exercise devices.

The user may continue to perform strength training exercises on the resistance training machine and adding to the workout information of the workout session. For example, the user may perform overhead presses and preacher curls, and the resistance training machine may record the user's performance and transmit the workout information to the workout server. In some examples, the user may then return to the treadmill to cooldown and finish their workout.

In some embodiments, the exercise devices are in data communication with a health and fitness platform that tracks and/or analyzes user workout information. Examples include the iFit platform from ICON Health and Fitness. The workout server receives the workout information from the exercise devices and stores the workout information. In some embodiments, once a user begins a workout routine, any additional workout information received is added to the active workout session. In some embodiments, the active workout session is closed and/or finalized when the workout routine instructions are completed by the user. For example, the active workout session is closed and/or finalized when the user completed a guided cross-training session on a treadmill and a rowing machine based on a workout routine received from the workout server.

In some embodiments, the active workout session will continue compiling workout information until the workout session is closed and/or finalized by the user. For example, the user may complete a guided bicycle ride on a stationary bicycle based on a workout routine received from the workout server, and then the user may change to a second exercise device (such as a resistance training machine) to perform additional strength training exercises selected by the user independent of a predetermined workout routine. Those additional strength training exercises may be recorded by the second exercise device and transmitted to the workout server to be compiled in the active workout session with the completed bicycle workout routine. The user may then close and/or finalize the workout session.

In the event the user forgets or chooses not to close and/or finalize the workout session, some embodiments according to the present disclosure include a timeout condition to close and/or finalize the workout session. For example, if the active workout session is not closed and/or finalized at the completion of a predetermined workout routine instruction or the user does not close and/or finalize the workout session through explicit input or command, the workout server may close and/or finalize the active workout session after not receiving additional workout information for a predetermined period of time. In some embodiments, the workout server may have a timeout condition of 2 hours or less. In some embodiments, the workout server may have a timeout condition of 1 hour or less. In some embodiments, the workout server may have a timeout condition of 30 minutes or less. In some embodiments, the workout server may have a timeout condition of 15 minutes or less. A timer used for the timeout condition may be reset based on receiving workout information from a sensor or exercise device.

In some embodiments, the timer is reset upon receiving login information or other detection of a user present on an exercise device. For example, a user may complete a first exercise on a first exercise device and leave the first exercise device to change to a second exercise device. If the time condition is 15 minutes, the workout session may timeout before workout server receives workout information from the second exercise device. The timer used for the timeout condition may be reset upon the second exercise device determining the user is present on/at the second exercise device to allow the user time to complete the desired exercise. For example, if the second exercise device transmits workout information upon completion of the exercise, a cardio exercise that requires 30 minutes would always cause a 30-minute timeout condition to expire unless the timer resets upon the second exercise device transmitting the user presence information.

Systems including exercise devices according to the present disclosure may include one or more sensors to collect workout information. In some embodiments, the first exercise device includes sensors to communicate workout information including duration of the workout, running speed, cycling speed, cadence, power output (Watts), weight of resistance, quantity of repetitions, rate of repetitions, range of motion, user weight, user height, user heartrate, other workout information, or combinations thereof. The sensors may communicate the workout information to the workout server directly (such as via a dedicated communication device associated with or integrated in the sensor), or the sensor(s) may communicate the workout information to a computing device of the first exercise device which, in turn, communicates the workout information to the workout server.

In some embodiments, the sensor(s) of the exercise device communicate the workout information to a workout server, and the workout service compiles the workout information with second workout information from sensor(s) of a second exercise device. In some embodiments, the second exercise device includes sensors to communicate workout information including duration of the workout, running speed, cycling speed, cadence, power output (Watts), weight of resistance, quantity of repetitions, rate of repetitions, range of motion, user weight, user height, user heartrate, other workout information, or combinations thereof. The sensors may communicate the workout information to the workout server directly (such as via a dedicated communication device associated with or integrated in the sensor), or the sensor(s) may communicate the workout information to a computing device of the second exercise device which, in turn, communicates the workout information to the workout server.

The workout information is communicated to the workout server via a network. In some embodiments, the network is the Internet or World Wide Web. In some embodiments, the network is a wide area network (WAN) or a local area network (LAN). For example, the network may communicate workout information between the exercise device(s) and the workout server at a remote location through one or more network nodes. In other examples, the workout server may be local to the exercise device(s), and the workout information is communicated to the workout server via a LAN.

The workout server is a computing device that receives and/or stores workout information in respective workout sessions associated with a user account. In some embodiments, the workout server stores the workout information at the workout server. In some embodiments, the workout server compiles the information and/or analyzes the workout information, and the workout server sends at least a portion of the workout information or a summary of the workout session to a client personal device or to exercise device(s) for viewing. In an example, the workout server generates a workout session report with at least some of the workout information and sends the workout session report to the user for viewing on a client device. The workout session report may be stored at the workout server.

The user account is associated with the user at the workout server, and the user may access the user account to upload workout information from a current workout session, view workout information, download workout information, analyze workout information, or combinations thereof. In some embodiments, the user account is associated with the user for a plurality of exercise devices and/or types of workouts. For example, the user account may allow a user to use a single profile to track workout information across aerobic workouts, strength training, flexibility, cross-training, or other workout types. In some embodiments, a single profile can allow the user to use a single login that is consistent across exercise devices and/or client devices.

In some embodiments, the user account is associated with a database of workout information, workout sessions, workout routines, workout preferences, or combinations thereof that are available to the exercise system to provide user-specific information and recommendations. In some examples, the workout information, workout sessions, workout routines, and workout preferences are determined from the user's history of completed exercises and workouts. In some examples, the workout information, workout sessions, workout routines, and workout preferences are received from direct user inputs, such as selecting particular preferences from a predetermined set of options or user selections of workout routines to add to a queue of future workouts to complete.

The user account may be associated with workout information, workout sessions, workout routines, workout preferences, or combinations thereof stored on the workout server. In some embodiments, the user account is associated with workout information, workout sessions, workout routines, workout preferences, or combinations thereof stored on a client personal device. A client personal device may be any electronic device that is local to the user and/or to the exercise device that is not the exercise device itself. For example, the client personal device may be a wearable client personal device (e.g., a watch, a chest worn heart rate monitor, a phone), an image capturing client personal device (e.g., a stationary or mobile camera), other client personal devices, or combinations thereof. In some embodiments, the user account is associated with workout information, workout sessions, workout routines, workout preferences, or combinations thereof stored on a client exercise device.

In some embodiments, at least a portion of the workout information, workout sessions, workout routines, workout preferences, or combinations thereof are stored on the workout server and accessible by a client personal device or client exercise device. For example, the client device(s) may access the workout information, workout sessions, workout routines, workout preferences, or combinations thereof stored on the workout server for display or other communication of the workout information, workout sessions, workout routines, workout preferences, or combinations thereof to the user. In at least one example, the client device(s) may access the workout information, workout sessions, workout routines, workout preferences, or combinations thereof stored on the workout server and combine or compile the workout information, workout sessions, workout routines, workout preferences, or combinations thereof stored on the workout server with the one or more of workout information, workout sessions, workout routines, workout preferences, or combinations thereof stored on the client device(s). For example, the client personal device may record heartrate workout information and access workout information of the workout session to combine the heartrate workout information with other workout information from the workout server. The client personal device may then display the combined results of the workout session or upload the combined results to the workout server.

In some embodiments, at least a portion of the workout information, workout sessions, workout routines, workout preferences, or combinations thereof are stored on a client device and accessible by the workout server. For example, the user may decide to run two miles (3.2 kilometers) before using a resistance training exercise device to perform a strength training workout routine. The user may carry on their person the personal client device (such as a smartphone or wearable device) during the run, and the personal client device may record workout information regarding the run while the user is away from the resistance training exercise device. When the user approaches the resistance training exercise device, in some embodiments, the resistance training exercise device may determine the user is present and communicate with the workout server.

In some embodiments, the workout server may receive workout information from the client personal device regarding a first portion of a workout session and from the resistance training exercise device regarding a second portion of the workout session. For example, the workout server may access the workout information collected by the client personal device to add the workout information of the run to any workout information collected by the resistance training exercise device during the selected strength training workout routine. In some embodiments, the workout server may receive workout information concurrently from both the client personal device and the resistance training exercise device regarding the workout session. While the user is performing the strength training workout routine, one or more sensors of the resistance training exercise device may collect workout information regarding repetitions, form, cadence, weight, range of motion, etc. while the client personal device measures the user's heartrate. The workout server may receive workout information concurrently from both the client personal device and the resistance training exercise device regarding the workout session.

In another example, a first exercise device may include internet connectivity to the workout server through a communication device integrated into the first exercise device and the second exercise device may include a local data connection device that allows the second exercise device to communicate with a client personal device. In some embodiments, the client personal device subsequently communicates the workout information collected by the second exercise device to the workout server.

Centralizing the workout information for one or more workout sessions at a workout server can allow for additional benefits, such as using machine learning models to customize future workout routines or recommendations based on the workout information stored on or accessed by the workout server. In some embodiments, the workout server is a general-purpose computer, and the workout server or other computing device connected to the workout server allows modularity and/or additional functionality beyond the processing resources and/or available software on the workout server. For example, the workout server, even when a general-purpose computer, may be updated at different cycles than the processing hardware of the exercise device. In at least one example, the workout server or other computing device is configured to execute at least one machine learning (ML) model to analyze and refine the ML model based upon the workout information and/or user inputs received by the ML model.

As illustrated in the foregoing discussion, the present disclosure utilizes a variety of terms to describe features and advantages of the machine learning model. As used herein, a "machine learning model" refers to a computer algorithm or model (e.g., a classification model, a regression model, a language model, an object detection model) that can be tuned (e.g., trained) based on training input to approximate unknown functions. For example, a machine learning model may refer to a neural network or other machine learning algorithm or architecture that learns and approximates complex functions and generate outputs based on a plurality of inputs provided to the machine learning model. In some embodiments, a machine learning system, model, or neural network described herein is an artificial neural network. In some embodiments, a machine learning system, model, or neural network described herein is a convolutional neural network. In some embodiments, a machine learning system, model, or neural network described herein is a recurrent neural network. In at least one embodiment, a machine learning system, model, or neural network described herein is a Bayes classifier. As used herein, a "machine learning system" may refer to one or multiple machine learning models that cooperatively generate one or more outputs based on corresponding inputs. For example, a machine learning system may refer to any system architecture having multiple discrete machine learning components that consider different kinds of information or inputs. In some embodiments, the ML model may allow for recommendations of workout routines, changes to repetitions, changes to weights or resistances, exercise duration or intensity, or for other changes based upon the user's workout information and/or aggregated workout information from a plurality of users.

In some embodiments, a method of compiling workout information for a workout session includes, at a workout server, receiving first login information from a first exercise device. The first login information may be provided to the first exercise device and subsequently received by the workout server in one or more ways.

For example, receiving the first login information from the first exercise device may include the first exercise device receiving near-field communication (NFC) login information from a user. In some embodiments, the NFC login information is received from an NFC user device that is uniquely associated with the user's account. For example, the NFC user device may be a key fob, a smartphone or other computing device such as a smartwatch, a wristband, a ring, or incorporated into an article of clothing or exercise equipment, such as the user's shoes, shirt, shorts, tights, or other article of clothing. The NFC user device may be brought into NFC range with a transceiver of the first exercise device, and the first exercise device may detect the presence of the NFC user device to uniquely identify the user. The first exercise device may then transmit the user account information to the workout server to associate the user of the first exercise device with a workout session.

In some examples, receiving the first login information from the first exercise device may include the first exercise device reading a barcode, QR code, or other machine-readable binary image code provided by a user. In some embodiments, the barcode login information is received from a user barcode that is uniquely associated with the user's account. For example, the user barcode may be printed on, displayed by, or integrated into a key fob, a smartphone or other computing device such as a smartwatch, a wristband, a ring, or incorporated into an article of clothing or exercise equipment, such as the user's shoes, shirt, shorts, tights, or other article of clothing. The user barcode may be brought into range of a camera or other image capture device of the first exercise device, and the first exercise device may detect the presence of the user barcode to uniquely identify the user. The first exercise device may then transmit the user account information to the workout server to associate the user of the first exercise device with a workout session.

In some examples, receiving the first login information from the first exercise device may include the first exercise device receiving biometric information from a user. In some embodiments, the biometric information is received from the user's body and is uniquely associated with the user's account. For example, receiving the biometric information may include fingerprint recognition, facial recognition, ocular recognition (including iris or ocular capillary recognition), palm recognition, voice recognition, or other biometric information methods. The user may place a portion of their body in contact with or near a biometric identification device (e.g., fingerprint scanner or video camera for facial recognition), and the first exercise device may detect the presence of the user to collect the biometric information and uniquely identify the user. The first exercise device may then transmit the user account information to the workout server to associate the user of the first exercise device with a workout session.

In some examples, receiving the first login information from the first exercise device may include the first exercise device receiving user login information from a conventional human interface device (HID) to login to the first exercise device. In some embodiments, the user login information is provided by user input to the HID device, and the user login information is uniquely associated with the user's account. For example, the HID device may be a keyboard, a number pad, a voice recognition device, a touchscreen or other touch-sensitive device, a mouse, a trackball, or other HID devices that allow the user to input the user login information. After receiving the user login information from the HID, the first exercise device may then transmit the user account information to the workout server to associate the user of the first exercise device with a workout session.

In some examples, receiving the first login information from the first exercise device may include the first exercise device receiving near-field communication (NFC) login information from a user. In some embodiments, the NFC login information is received from a data communication with a paired client device that is uniquely associated with the user's account. For example, the paired client device may be a key fob, a smartphone or other computing device such as a smartwatch, a wristband, a ring, or incorporated into an article of clothing or exercise equipment, such as the user's shoes, shirt, shorts, tights, or other article of clothing. The paired client device may be brought into communication range with a transceiver of the first exercise device, and the first exercise device may detect the presence of the paired client device to uniquely identify the user. The first exercise device may then transmit the user account information to the workout server to associate the user of the first exercise device with a workout session.

In some embodiments, the paired client device communicates with the first exercise device using a wireless data communication protocol. For example, the client device and the first exercise device may communicate through a Bluetooth data connection. In some examples, the client device and the first exercise device may communicate through a Wi-Fi direct data connection. In some examples, the client device and the first exercise device may communicate through a proprietary data connection protocol.

In some examples, receiving the first login information from the first exercise device may include the first exercise device receiving a selection by a user of a saved user account from one or more user accounts saved locally on the first exercise device. In some embodiments, the selected saved user account is uniquely associated with the user's account. For example, the first exercise device may have a plurality of saved user accounts that represent each member of a family in a household. The plurality of saved user accounts may be saved locally on the first exercise device. The first exercise device may present to the user a list of available saved user accounts, and the user may select (such as by a touchscreen or other HID) the saved user account associated with the user. The first exercise device may then transmit the user account information to the workout server to associate the user of the first exercise device with a workout session.

In some embodiments, the user subsequently begins a workout by engaging with the first exercise device. In some embodiments, the user may browse or search for a predetermined workout routine, which the first exercise device or other device may then present to the user. The method further includes receiving first workout information from the first exercise device. In some embodiments, the first exercise device measures the workout information of the user engaged with the first exercise device.

In some embodiments, the first exercise device receives the workout information of the user engaged with the first exercise device from a wearable device or other electronic device that measures the workout information and relays the workout information to the first exercise device. The first exercise device may include sensors to record and/or communicate workout information including duration of the workout, running speed, cycling speed, cadence, power output (Watts), weight of resistance, quantity of repetitions, rate of repetitions, range of motion, user weight, user height, user heartrate, other workout information, or combinations thereof. The sensors of the first exercise device may communicate the workout information to the workout server directly (such as via a dedicated communication device associated with or integrated in the sensor), or the sensor(s) may communicate the workout information to a computing device of the first exercise device which, in turn, communicates the workout information to the workout server.

Upon receiving the first workout information from the first exercise device, the workout server assigns the first workout information to a workout session associated with the user account. The active workout session may include any workout information associated with the user account that is received by the workout server. In some embodiments, the active workout session remains active for a predetermined period of time since the last workout information was received or until a closure instruction is received from an exercise device. For example, the workout session may remain active based on a timeout condition that is based upon when the last workout information was received. In some embodiments, the workout session will close upon receiving a termination instruction from the exercise device. For example, the user may select an option on the exercise device to terminate the workout session, and the exercise device transmits the termination instruction to the workout server. The workout server may then terminate the workout session, disallowing any further workout information to be added to the workout session. In some examples, the termination instruction may terminate a workout session irrespective of a timeout condition.

In some embodiments, the workout server may have a timeout condition of 2 hours or less. In some embodiments, the workout server may have a timeout condition of 1 hour or less. In some embodiments, the workout server may have a timeout condition of 30 minutes or less. In some embodiments, the workout server may have a timeout condition of 15 minutes or less. A timer used for the timeout condition may be reset based on receiving workout information from a sensor or exercise device.

In some embodiments, the timer is reset upon receiving login information or other detection of a user present on an exercise device. For example, a user may complete a first exercise on a first exercise device and leave the first exercise device to change to a second exercise device. If the time condition is 15 minutes, the workout session may timeout before workout server receives workout information from the second exercise device. The timer used for the timeout condition may be reset upon the second exercise device determining the user is present on/at the second exercise device to allow the user time to complete the desired exercise. For example, if the second exercise device transmits workout information upon completion of the exercise, a cardio exercise that requires 30 minutes would always cause a 30-minute timeout condition to expire unless the timer resets upon the second exercise device transmitting the user presence information.

The method further includes receiving second login information from a second exercise device. In at least one embodiment, the second login information is received from the second exercise device within a timeout condition. In some embodiments, the second login information is received before a termination instruction is received at the workout server. The second login information from the second exercise device is login information that is associated with the same user account as the first login information, but the second login information may be collected by the second exercise device in the same or different manner than the first login information is collected by the first exercise device. For example, the first login information may be provided by the user to the first exercise device via an NFC user device, and the second login information may be provided by the user to the second exercise device via a QR code. In another example, the first login information may be provided by the user to the first exercise device by selecting a locally saved user account, and the second login information may be provided by the user to the second exercise device by selecting a locally saved user account. In another example, the first login information may be provided by the user to the first exercise device by a paired client device, and the second login information may be provided by the user to the second exercise device by the paired client device.

Receiving the second login information from the first exercise device may include the second exercise device receiving NFC login information from a user. In some embodiments, the NFC login information is received from an NFC user device that is uniquely associated with the user's account. For example, the NFC user device may be a key fob, a smartphone or other computing device such as a smartwatch, a wristband, a ring, or incorporated into an article of clothing or exercise equipment, such as the user's shoes, shirt, shorts, tights, or other article of clothing. The NFC user device may be brought into NFC range with a transceiver of the second exercise device, and the second exercise device may detect the presence of the NFC user device to uniquely identify the user. The second exercise device may then transmit the user account information to the workout server to associate the user of the second exercise device with the workout session.

In some examples, receiving the second login information from the second exercise device may include the second exercise device reading a barcode, QR code, or other machine-readable binary image code provided by a user. In some embodiments, the barcode login information is received from a user barcode that is uniquely associated with the user's account. For example, the user barcode may be printed on, displayed by, or integrated into a key fob, a smartphone or other computing device such as a smartwatch, a wristband, a ring, or incorporated into an article of clothing or exercise equipment, such as the user's shoes, shirt, shorts, tights, or other article of clothing. The user barcode may be brought into range of a camera or other image capture device of the second exercise device, and the second exercise device may detect the presence of the user barcode to uniquely identify the user. The second exercise device may then transmit the user account information to the workout server to associate the user of the second exercise device with the workout session.

In some examples, receiving the second login information from the second exercise device may include the second exercise device receiving biometric information from a user. In some embodiments, the biometric information is received from the user's body and is uniquely associated with the user's account. For example, receiving the biometric information may include fingerprint recognition, facial recognition, ocular recognition (including iris or ocular capillary recognition), palm recognition, voice recognition, or other biometric information methods. The user may place a portion of their body in contact with or near a biometric identification device (e.g., fingerprint scanner or video camera for facial recognition), and the second exercise device may detect the presence of the user to collect the biometric information and uniquely identify the user. The second exercise device may then transmit the user account information to the workout server to associate the user of the second exercise device with a workout session.

In some examples, receiving the second login information from the second exercise device may include the second exercise device receiving user login information from a conventional HID to login to the second exercise device. In some embodiments, the user login information is provided by user input to the HID device, and the user login information is uniquely associated with the user's account. For example, the HID device may be a keyboard, a number pad, a voice recognition device, a touchscreen or other touch-sensitive device, a mouse, a trackball, or other HID devices that allow the user to input the user login information. After receiving the user login information from the HID, the second exercise device may then transmit the user account information to the workout server to associate the user of the second exercise device with the workout session.

In some examples, receiving the second login information from the second exercise device may include the second exercise device receiving near-field communication (NFC) login information from a user. In some embodiments, the NFC login information is received from a data communication with a paired client device that is uniquely associated with the user's account. For example, the paired client device may be a key fob, a smartphone or other computing device such as a smartwatch, a wristband, a ring, or incorporated into an article of clothing or exercise equipment, such as the user's shoes, shirt, shorts, tights, or other article of clothing. The paired client device may be brought into communication range with a transceiver of the second exercise device, and the second exercise device may detect the presence of the paired client device to uniquely identify the user. The second exercise device may then transmit the user account information to the workout server to associate the user of the second exercise device with a workout session.

In some embodiments, the paired client device communicates with the second exercise device using a wireless data communication protocol. For example, the client device and the second exercise device may communicate through a Bluetooth data connection. In some examples, the client device and the second exercise device may communicate through a Wi-Fi direct data connection. In some examples, the client device and the second exercise device may communicate through a proprietary data connection protocol.

In some examples, receiving the second login information from the second exercise device may include the second exercise device receiving a selection by a user of a saved user account from one or more user accounts saved locally on the second exercise device. In some embodiments, the selected saved user account is uniquely associated with the user's account. For example, the second exercise device may have a plurality of saved user accounts that represent each member of a family in a household. The plurality of saved user accounts may be saved locally on the second exercise device. The second exercise device may present to the user a list of available saved user accounts, and the user may select (such as by a touchscreen or other HID) the saved user account associated with the user. The second exercise device may then transmit the user account information to the workout server to associate the user of the second exercise device with a workout session.

The method further includes receiving, at the workout server, second workout information from the second exercise device. In some embodiments, the second exercise device measures the second workout information of the user engaged with the second exercise device.

In some embodiments, the second exercise device receives the workout information of the user engaged with the second exercise device from a wearable device or other electronic device that measures the workout information and relays the workout information to the second exercise device. The second exercise device may include a sensor(s) to record and/or communicate workout information including duration of the workout, running speed, cycling speed, cadence, power output (Watts), weight of resistance, quantity of repetitions, rate of repetitions, range of motion, user weight, user height, user heartrate, other workout information, or combinations thereof. The sensors of the second exercise device may communicate the second workout information to the workout server directly (such as via a dedicated communication device associated with or integrated in the sensor), or the sensor(s) may communicate the second workout information to a computing device of the second exercise device which, in turn, communicates the second workout information to the workout server. Upon receiving the second workout information from the second exercise device, the workout server assigns the second workout information to the active workout session associated with the user account.

In at least one embodiment, the method further includes terminating the active workout session. The active workout session may be terminated by expiration of a timeout condition, by completion of a selected workout routine, or by receipt of a termination instruction from an exercise device. In at least one example, the workout session remains active after completing a workout routine, as the user may desire to select an addition workout routine or continue the workout session with ad hoc exercises.

Workout information from the workout session may be presented to the user and/or recorded for later viewing or analysis. For example, the workout information for the workout session may be presented to the user on a display of the most recently used exercise device, via a web portal, via a native application on a client device, or through another presentation mechanism. The user may then be able to better understand his or her fitness, progression, or goals. The workout information may be input into a ML model to better suggest or adapt workout routines for the user. By allowing a user to transition between multiple exercise devices within a single active workout session, a workout system can provide a user a more complete workout with greater variety to ensure an effective, efficient, and enjoyable workout.

Following are sections describing various embodiments of the present disclosure:

A1. A method of compiling workout information in a workout session, the method comprising:
  at a workout server:
    receiving, via a network, first login information from a first exercise device;
    receiving, via the network, first workout information from the first exercise device;
    recording the first workout information in an active workout session;
    receiving, via the network, second login information from a second exercise device;
    receiving, via the network, second workout information from the second exercise device; and
    recording the second workout information in the active workout session.

A2. The method of section A1, further comprising terminating the active workout session upon expiration of a timeout condition.

A3. The method of any of sections A1 or A2, further comprising terminating the active workout session upon receiving a termination instruction from the second exercise device.

A4. The method of any of sections A1-A3, wherein the first login information includes NFC login information.

A5. The method of any of sections A1-A4, wherein the first login information includes barcode login information.

A6. The method of any of sections A1-A5, wherein the first login information includes biometric login information.

A7. The method of any of sections A1-A6, wherein the first login information includes electromagnetic login information.

A8. The method of any of sections A1-7, further comprising transmitting at least part of a workout routine to the first exercise device for presentation to a user.

A9. The method of section A8, further comprising transmitting at least another part of the workout routine to the second exercise device for presentation to a user.

A10. The method of any of sections A1-A9, further comprising accessing a user account associated with the first login information and recording the active workout session associated with the user account.

A11. The method of section 10, wherein the user account includes user information indicating a plurality of available exercise devices associated with the user account.

A12. The method of section 11, further comprising suggesting a workout routine including exercises on at least the first exercise device and the second exercise device of the plurality of available exercise devices.

B1. A system for recording workout information, the system comprising:
  a first exercise device in communication with a network;
  a second exercise device in communication with the network; and
  a workout server in communication with the first exercise device and the second exercise device via the network, the workout server including:
    a processor, and
    a hardware storage device having instructions stored thereon that, when executed by the processor, cause the workout server to:

receive, via the network, first login information from the first exercise device, receive, via the network, first workout information from the first exercise device, record the first workout information in an active workout session;

receive, via the network, second login information from the second exercise device;

receive, via the network, second workout information from the second exercise device; and record the second workout information in the active workout session.

B2. The system of section B1, wherein the first exercise device and second exercise device are different types of exercise devices.

B3. The system of any of sections B1 or B2, wherein at least one of the first exercise device and the second exercise device is an exercise bicycle.

B4. The system of any of sections B1-B3, wherein at least one of the first exercise device and the second exercise device is a treadmill.

B5. The system of any of sections B1-B4, wherein at least one of the first exercise device and the second exercise device is a resistance training exercise device.

C1. A method of compiling workout information in a workout session, the method comprising:

at a workout server:

receiving, via a network, first login information from a first client device;

receiving, via the network, first workout information from the first client device;

recording the first workout information in an active workout session;

receiving, via the network, second login information from a second client device;

receiving, via the network, second workout information from the second client device; and recording the second workout information in the active workout session.

C2. The method of section C1, wherein the first client device is an electronic device having at least one sensor to collect the first workout information.

C3. The method of section C2, wherein the second client device is an exercise device.

D1. A method of compiling workout information in a workout session, the method comprising:

at a workout server:

receiving, via a network, first login information from a first exercise device;

receiving, via the network, first workout information from the first exercise device;

recording the first workout information in an active workout session;

receiving, via the network, second login information from a second exercise device, wherein the second login information includes at least one of NFC login information, barcode login information, biometric login information, and electromagnetic login information;

receiving, via the network, second workout information from the second exercise device; and recording the second workout information in the active workout session.

E1. A system for recording workout information, the system comprising:

a first exercise device in communication with a network;

a second exercise device in communication with the network; and a workout server in communication with the first exercise device and the second exercise device via the network, the workout server including:

a processor, and a hardware storage device having instructions stored thereon that, when executed by the processor, cause the workout server to:

receive, via the network, first login information from the first exercise device, receive, via the network, first workout information from the first exercise device, record the first workout information in an active workout session;

receive, via the network, second login information from the second exercise device, wherein the second login information includes at least one of NFC login information, barcode login information, biometric login information, and electromagnetic login information;

receive, via the network, second workout information from the second exercise device; and record the second workout information in the active workout session.

F1. A method having any or each permutation of features recited in sections A1 to E1.

G1. An assembly/system/device having any or each permutation of features recited in sections A1 to E1.

H1. Any system, assembly, component, subcomponent, process, element, or portion thereof, as described or illustrated.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the scope of the present disclosure, and that various changes, substitutions, and alterations may be made to embodiments disclosed herein without departing from the scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

It should be understood that any directions or reference frames in the preceding description are merely relative directions or movements. For example, any references to "front" and "back" or "top" and "bottom" or "left" and "right" are merely descriptive of the relative position or movement of the related elements.

The present disclosure may be embodied in other specific forms without departing from its characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A method of compiling workout information in a workout session, the method comprising:
    detecting, at a first exercise device, a presence of a user associated with user account information;
    measuring, at the first exercise device, first workout information for the user;
    receiving, at a workout server via a network, first login the user account information from the first exercise device;
    receiving, at the workout server via the network, the first workout information from the first exercise device;
    storing, at the workout server, the first workout information in the workout session based on receiving the user account information and on receiving the first workout information from the first exercise device;
    detecting, at a second exercise device, the presence of the user associated with the user account information, wherein detecting the presence of the user is based on receiving at least one of near-field communication (NFC) login information, barcode login information, biometric login information, and electromagnetic login information;
    measuring, at the second exercise device, second workout information for the user;
    receiving, at the workout server via the network, the user account information from the second exercise device;
    receiving, at the workout server via the network, the second workout information from the second exercise device;
    storing, at the workout server, the second workout information in the workout session based on receiving the user account information and on receiving the second workout information from the second exercise device; and
    displaying, on a display of the second exercise device, both the first workout information and the second workout information associated with the workout session.

2. The method of claim 1, further comprising terminating the workout session upon expiration of a timeout condition.

3. The method of claim 1, further comprising terminating the workout session upon receiving a termination instruction from the second exercise device.

4. The method of claim 1, wherein detecting the presence of the user at the first exercise device is based on receiving at least one of NFC login information, barcode login information, biometric login information, and electromagnetic login information.

5. The method of claim 1, wherein the first exercise device detects the presence of the user in the same manner as the second exercise device detects the presence of the user.

6. The method of claim 1, wherein the first exercise device detects the presence of the user in a different manner as the second exercise device detects the presence of the user.

7. The method of claim 1, further comprising transmitting at least part of a workout routine to the first exercise device for presentation to the user.

8. The method of claim 7, further comprising transmitting at least another part of the workout routine to the second exercise device for presentation to the user.

9. The method of claim 1, further comprising accessing a user account associated with the user account information and storing the workout session associated with the user account.

10. The method of claim 9, wherein the user account includes user information indicating a plurality of available exercise devices associated with the user account, wherein the plurality of available exercise devices comprises at least the first exercise device and the second exercise device.

11. The method of claim 10, further comprising suggesting a workout routine including exercises on at least the first exercise device and the second exercise device of the plurality of available exercise devices.

12. A system for compiling workout information in a workout session, the system comprising:
    a first exercise device in communication with a network;
    a second exercise device in communication with the network; and
    a workout server in communication with the first exercise device and the second exercise device via the network, the workout server including:
        a processor, and
        a hardware storage device having instructions stored thereon that, when executed by the processor, cause the workout server to:
            receive, via the network, user account information from the first exercise device, wherein receiving the user account information is based on detection, by the first exercise device, of a presence of a user associated with the user account information;
            receive, via the network, first workout information from the first exercise device, wherein the first workout information is measured for the user by the first exercise device;
            store the first workout information in the workout session based on reception of the user account information and on reception of the first workout information from the first exercise device;
            receive, via the network, the user account information from the second exercise device, wherein the user account information is received based on detection, by the second exercise device, of the presence of the user associated with the user account information, and wherein the presence of the user at the second exercise device is detected based on at least one of NFC login information, barcode login information, biometric login information, and electromagnetic login information;
            receive, via the network, second workout information from the second exercise device, wherein the second workout information is measured for the user by the second exercise device;
            store the second workout information in the workout session based on reception of the user account information and on reception of the second workout information from the second exercise device; and display, on a display of the second exercise device, both the first workout information and the second workout information associated with the workout session.

13. The system of claim 12, wherein the first exercise device and the second exercise device are different types of exercise devices.

14. The system of claim 12, wherein at least one of the first exercise device and the second exercise device is an exercise bicycle.

15. The system of claim 12, wherein at least one of the first exercise device and the second exercise device is a treadmill.

16. The system of claim 12, wherein at least one of the first exercise device and the second exercise device is a resistance training exercise device.

17. A method of compiling workout information in a workout session, the method comprising:

measuring, at a first client device, first workout information for a user;

receiving, at a workout server via a network, user account information associated with the user from the first client device;

receiving, at the workout server via the network, the first workout information from the first client device;

storing the first workout information in the workout session based on receiving the user account information and on receiving the first workout information from the first client device;

detecting, at a second client device, a presence of the user associated with the user account information, wherein detecting the presence of the user is based on receiving at least one of NFC login information, barcode login information, biometric login information, and electromagnetic login information;

measuring, at the second client device, second workout information for the user;

receiving, at the workout server via the network, the user account information from the second client device;

receiving, at the workout server via the network, the second workout information from the second client device;

storing the second workout information in the workout session based on receiving the user account information and on receiving the second workout information from the second client device; and displaying, on a display of the first client device, the second client device, or both, both the first workout information and the second workout information associated with the workout session.

18. The method of claim 17, wherein the first client device is an electronic device having at least one sensor to collect the first workout information.

19. The method of claim 18, wherein the second client device is an exercise device.

* * * * *